(12) United States Patent
Sharkey et al.

(10) Patent No.: US 11,006,992 B2
(45) Date of Patent: *May 18, 2021

(54) METHOD FOR TREATING JOINT PAIN AND ASSOCIATED INSTRUMENTS

(71) Applicant: ZIMMER KNEE CREATIONS, INC., Exton, PA (US)

(72) Inventors: Peter F. Sharkey, Villanova, PA (US); Charles F. Leinberry, Chester Springs, PA (US); Steven B. Cohen, Media, PA (US); Charanpreet S. Bagga, Basking Ridge, NJ (US); Erik M. Erbe, Rancho Santa Fe, CA (US)

(73) Assignee: ZIMMER KNEE CREATIONS, INC., Exton, PA (US)

(*) Notice: Subject to any disclaimer, the term of this patent is extended or adjusted under 35 U.S.C. 154(b) by 165 days.

This patent is subject to a terminal disclaimer.

(21) Appl. No.: 16/229,737

(22) Filed: Dec. 21, 2018

(65) Prior Publication Data

US 2019/0133663 A1 May 9, 2019

Related U.S. Application Data

(63) Continuation of application No. 15/606,714, filed on May 26, 2017, now Pat. No. 10,271,883, which is a
(Continued)

(51) Int. Cl.
*A61B 17/88* (2006.01)
*A61B 17/17* (2006.01)
(Continued)

(52) U.S. Cl.
CPC ...... *A61B 17/8805* (2013.01); *A61B 17/1764* (2013.01); *A61F 2/28* (2013.01);
(Continued)

(58) Field of Classification Search
CPC .. A61B 17/17; A61B 17/1703; A61B 17/1764
See application file for complete search history.

(56) References Cited

U.S. PATENT DOCUMENTS

| 2,697,433 | A | 12/1954 | Zehnder |
| 3,913,187 | A | 10/1975 | Okuida |

(Continued)

FOREIGN PATENT DOCUMENTS

| CN | 101048111 A | 10/2007 |
| CN | 101102724 A | 1/2008 |

(Continued)

OTHER PUBLICATIONS

"European Application Serial No. 10832259.5, Response filed May 10, 2018 to Extended European Search Report dated Oct. 24, 2017", 105 pgs.
(Continued)

*Primary Examiner* — Andrew Yang
(74) *Attorney, Agent, or Firm* — Schwegman Lundberg & Woessner, P.A.

(57) ABSTRACT

The embodiments provide provides devices, instruments, and associated methods for treating joint pain. A joint is evaluated using magnetic resonance imaging to detect any defects in the subchondral bone. For example, using T2-weighted MRI images, bone marrow lesions or edemas can be identified, and using T1-weighted MRI images, associated regions of sclerotic bone adjacent to the bone marrow lesion can be identified. The treatment method may involve introducing a bone void filler material at the site to address the bone marrow lesion or edema, and/or drilling and inserting an implant to address the sclerotic bone, bone marrow lesion or edema, and insufficiency or stress fractures. An access path is mapped to a location in the subchondral region where the insufficiency fracture resides. The access path attempts to preserve an articular surface of the
(Continued)

joint. A reinforcing member that stabilizes the insufficiency fracture is then implanted via the access path.

26 Claims, 22 Drawing Sheets

Related U.S. Application Data continuation of application No. 15/166,345, filed on May 27, 2016, now Pat. No. 9,730,744, which is a continuation of application No. 14/724,160, filed on May 28, 2015, now Pat. No. 9,351,835, which is a continuation of application No. 14/454,298, filed on Aug. 7, 2014, now Pat. No. 9,119,721, which is a continuation of application No. 12/950,097, filed on Nov. 19, 2010, now Pat. No. 8,821,504.

(60) Provisional application No. 61/263,170, filed on Nov. 20, 2009.

(51) Int. Cl.
*A61F 2/28* (2006.01)
*A61F 2/38* (2006.01)
*A61F 2/30* (2006.01)
*A61B 17/68* (2006.01)
*A61B 17/90* (2006.01)

(52) U.S. Cl.
CPC .............. *A61F 2/30* (2013.01); *A61F 2/38* (2013.01); *A61B 17/17* (2013.01); *A61B 17/1703* (2013.01); *A61B 17/1742* (2013.01); *A61B 17/1775* (2016.11); *A61B 17/1778* (2016.11); *A61B 17/68* (2013.01); *A61B 17/8802* (2013.01); *A61B 17/8872* (2013.01); *A61B 2017/90* (2013.01); *A61F 2002/30001* (2013.01)

(56) References Cited

U.S. PATENT DOCUMENTS

| | | |
|---|---|---|
| 3,988,783 A | 11/1976 | Treace |
| 4,037,592 A | 7/1977 | Kronner |
| 4,108,165 A | 8/1978 | Kopp et al. |
| 4,360,012 A | 11/1982 | McHarrie et al. |
| 4,653,487 A | 3/1987 | Maale |
| 4,781,182 A | 11/1988 | Purnell et al. |
| 4,815,454 A | 3/1989 | Dozier, Jr. |
| 4,834,757 A | 5/1989 | Brantigan |
| 4,883,048 A | 11/1989 | Purnell et al. |
| 4,911,153 A | 3/1990 | Border |
| 4,920,958 A | 5/1990 | Walt et al. |
| 4,964,861 A | 10/1990 | Agee et al. |
| 5,098,383 A | 3/1992 | Hemmy et al. |
| 5,163,940 A | 11/1992 | Bourque |
| 5,178,164 A | 1/1993 | Allen |
| 5,247,934 A | 9/1993 | Wehrli et al. |
| 5,298,254 A | 3/1994 | Prewett et al. |
| 5,324,295 A | 6/1994 | Shapiro |
| 5,342,363 A | 8/1994 | Richelsoph |
| 5,370,646 A | 12/1994 | Reese et al. |
| 5,439,684 A | 8/1995 | Prewett et al. |
| 5,458,602 A | 10/1995 | Goble et al. |
| 5,514,137 A | 5/1996 | Coutts |
| 5,556,429 A | 9/1996 | Felt |
| 5,595,193 A | 1/1997 | Walus et al. |
| 5,609,636 A | 3/1997 | Kohrs et al. |
| 5,618,549 A | 4/1997 | Patat et al. |
| 5,681,320 A | 10/1997 | McGuire |
| 5,741,266 A | 4/1998 | Moran et al. |
| 5,743,916 A | 4/1998 | Greenberg et al. |
| 5,755,809 A | 5/1998 | Cohen et al. |
| 5,766,221 A | 6/1998 | Benderev et al. |
| 5,827,289 A | 10/1998 | Reiley et al. |
| 5,868,749 A | 2/1999 | Reed |
| 5,888,220 A | 3/1999 | Felt et al. |
| 5,891,150 A | 4/1999 | Chan |
| 5,928,239 A | 7/1999 | Mirza |
| 5,968,047 A | 10/1999 | Reed |
| 5,968,050 A | 10/1999 | Torrie |
| 5,972,015 A | 10/1999 | Scribner et al. |
| 6,010,502 A | 1/2000 | Bagby |
| 6,019,776 A | 2/2000 | Preissman et al. |
| 6,036,696 A | 3/2000 | Lambrecht et al. |
| 6,039,742 A | 3/2000 | Krettek et al. |
| 6,048,346 A | 4/2000 | Reiley et al. |
| 6,066,154 A | 5/2000 | Reiley et al. |
| 6,110,211 A | 8/2000 | Weiss |
| 6,111,164 A | 8/2000 | Rainey et al. |
| 6,120,511 A | 9/2000 | Chan |
| 6,140,452 A | 10/2000 | Felt et al. |
| 6,143,030 A | 11/2000 | Schroder |
| 6,162,225 A | 12/2000 | Gertzman et al. |
| 6,214,013 B1 | 4/2001 | Lambrecht et al. |
| 6,235,043 B1 | 5/2001 | Reiley et al. |
| 6,241,734 B1 | 6/2001 | Scribner et al. |
| 6,248,110 B1 | 6/2001 | Reiley et al. |
| 6,248,131 B1 | 6/2001 | Felt et al. |
| 6,254,605 B1 | 7/2001 | Howell |
| 6,267,770 B1 | 7/2001 | Truwit |
| 6,270,528 B1 | 8/2001 | McKay |
| 6,283,942 B1 | 9/2001 | Staehlin et al. |
| 6,285,901 B1 | 9/2001 | Taicher et al. |
| 6,287,313 B1 | 9/2001 | Sasso |
| 6,294,187 B1 | 9/2001 | Boyce et al. |
| 6,306,177 B1 | 10/2001 | Felt et al. |
| 6,342,056 B1 | 1/2002 | Mac-Thiong et al. |
| 6,358,251 B1 | 3/2002 | Mirza |
| 6,368,322 B1 | 4/2002 | Luks et al. |
| 6,395,007 B1 | 5/2002 | Bhatnagar et al. |
| 6,398,811 B1 | 6/2002 | McKay |
| 6,423,083 B2 | 7/2002 | Reiley et al. |
| 6,486,232 B1 | 11/2002 | Wise et al. |
| 6,506,192 B1 | 1/2003 | Gertzman et al. |
| 6,506,785 B2 | 1/2003 | Evans et al. |
| 6,520,969 B2 | 2/2003 | Lambrecht et al. |
| 6,527,773 B1 | 3/2003 | Lin et al. |
| 6,533,794 B2 | 3/2003 | Chakeres |
| 6,564,083 B2 | 5/2003 | Stevens |
| 6,607,561 B2 | 8/2003 | Brannon |
| 6,613,054 B2 | 9/2003 | Scribner et al. |
| 6,645,213 B2 | 11/2003 | Sand et al. |
| 6,663,647 B2 | 12/2003 | Reiley et al. |
| 6,719,761 B1 | 4/2004 | Reiley et al. |
| 6,726,691 B2 | 4/2004 | Osorio et al. |
| 6,730,124 B2 | 5/2004 | Steiner |
| 6,746,451 B2 | 6/2004 | Middleton et al. |
| 6,767,369 B2 | 7/2004 | Boyer, II et al. |
| 6,814,736 B2 | 11/2004 | Reiley et al. |
| 6,827,720 B2 | 12/2004 | Leali |
| 6,863,672 B2 | 3/2005 | Reiley et al. |
| 6,863,899 B2 | 3/2005 | Koblish et al. |
| 6,869,434 B2 | 3/2005 | Choi |
| 6,875,212 B2 | 4/2005 | Shaolian et al. |
| 6,887,246 B2 | 5/2005 | Bhatnagar et al. |
| 6,899,719 B2 | 5/2005 | Reiley et al. |
| 6,923,813 B2 | 5/2005 | Phillips |
| 6,917,827 B2 | 7/2005 | Kienzle, III |
| 6,918,916 B2 | 7/2005 | Gobel et al. |
| 6,979,341 B2 | 12/2005 | Scribner et al. |
| 6,981,981 B2 | 1/2006 | Reiley |
| 7,001,431 B2 | 2/2006 | Bao et al. |
| 7,029,477 B2 | 4/2006 | Grimm |
| 7,063,701 B2 | 6/2006 | Michelson |
| 7,063,702 B2 | 6/2006 | Michelson |
| 7,087,082 B2 | 8/2006 | Paul et al. |
| 7,094,239 B1 | 8/2006 | Michelson |
| 7,115,146 B2 | 10/2006 | Boyer, II et al. |
| 7,144,414 B2 | 12/2006 | Harvie et al. |
| 7,153,305 B2 | 12/2006 | Johnson et al. |
| 7,153,306 B2 | 12/2006 | Ralph et al. |

(56) References Cited

U.S. PATENT DOCUMENTS

| | | |
|---|---|---|
| 7,153,307 B2 | 12/2006 | Scribner |
| 7,155,306 B2 | 12/2006 | Haitin et al. |
| 7,160,305 B2 | 1/2007 | Schmieding |
| 7,192,431 B2 | 3/2007 | Hangody et al. |
| 7,226,481 B2 | 6/2007 | Kuslich |
| 7,241,303 B2 | 7/2007 | Reiss et al. |
| 7,250,055 B1 | 7/2007 | Vandewalle |
| 7,252,671 B2 | 8/2007 | Scribner et al. |
| 7,261,716 B2 | 8/2007 | Strobel et al. |
| 7,261,720 B2 | 8/2007 | Stevens et al. |
| 7,313,430 B2 | 12/2007 | Urquhart et al. |
| 7,399,306 B2 | 7/2008 | Reiley et al. |
| 7,410,947 B2 | 8/2008 | Rueger et al. |
| 7,448,264 B2 | 11/2008 | Boyce et al. |
| 7,458,977 B2 | 12/2008 | McGinley et al. |
| 7,468,075 B2 | 12/2008 | Lang et al. |
| 7,476,226 B2 | 1/2009 | Weikel et al. |
| 7,477,770 B2 | 1/2009 | Wehrli et al. |
| 7,485,119 B2 | 2/2009 | Thelen et al. |
| 7,488,348 B2 | 2/2009 | Truncale et al. |
| 7,491,205 B1 | 2/2009 | Michelson |
| 7,507,240 B2 | 3/2009 | Olsen |
| 7,534,226 B2 | 5/2009 | Mernoe et al. |
| 7,545,964 B2 | 6/2009 | Lang et al. |
| 7,550,007 B2 | 6/2009 | Malinin |
| 7,550,011 B2 | 6/2009 | McKay et al. |
| 7,556,295 B2 | 7/2009 | Holzheu |
| 7,559,932 B2 | 7/2009 | Truckai et al. |
| 7,575,578 B2 | 8/2009 | Wetzler et al. |
| 7,594,917 B2 | 9/2009 | Whittaker et al. |
| 7,608,097 B2 | 10/2009 | Kyle |
| 7,608,098 B1 | 10/2009 | Stone et al. |
| 7,643,664 B2 | 1/2010 | Wehrli et al. |
| 7,682,378 B2 | 3/2010 | Truckai et al. |
| 7,704,256 B2 | 4/2010 | Sand et al. |
| 7,708,742 B2 | 5/2010 | Scribner et al. |
| 7,713,273 B2 | 5/2010 | Krueer et al. |
| 7,731,720 B2 | 6/2010 | Sand et al. |
| 7,753,963 B2 | 7/2010 | Boyer, II et al. |
| 7,769,213 B2 | 8/2010 | Gregory et al. |
| 7,771,431 B2 | 8/2010 | Scribner et al. |
| 7,789,912 B2 | 9/2010 | Manzi et al. |
| 7,811,290 B2 | 10/2010 | Rabiner |
| 7,837,733 B2 | 11/2010 | Collins et al. |
| 7,837,740 B2 | 11/2010 | Semler et al. |
| 7,840,247 B2 | 11/2010 | Liew et al. |
| 7,846,206 B2 | 12/2010 | Oglaza et al. |
| 7,879,038 B2 | 2/2011 | Reiley et al. |
| 7,879,099 B2 | 2/2011 | Zipnick |
| 7,887,543 B2 | 2/2011 | Sand et al. |
| 7,887,546 B2 | 2/2011 | Gil |
| 7,896,885 B2 | 3/2011 | Miniaci et al. |
| 7,901,408 B2 | 3/2011 | Ek |
| 7,901,457 B2 | 3/2011 | Truncale et al. |
| 7,905,924 B2 | 3/2011 | White |
| 7,914,539 B2 | 3/2011 | Stone et al. |
| 7,927,339 B2 | 4/2011 | Ralph et al. |
| 7,931,840 B2 | 4/2011 | Michelson |
| 7,938,835 B2 | 5/2011 | Boucher et al. |
| 7,959,638 B2 | 6/2011 | Osorio et al. |
| 7,985,231 B2 | 7/2011 | Sankaran |
| 8,029,511 B2 | 10/2011 | Bowman et al. |
| 8,062,364 B1 | 11/2011 | Sharkey et al. |
| 8,070,753 B2 | 12/2011 | Truckai et al. |
| 8,092,480 B2 | 1/2012 | Layne |
| 8,133,226 B2 | 3/2012 | Chou et al. |
| 8,142,462 B2 | 3/2012 | Middleton |
| 8,152,813 B2 | 4/2012 | Osorio et al. |
| 8,168,692 B2 | 5/2012 | Wenz |
| 8,187,327 B2 | 5/2012 | Edidin et al. |
| 8,246,681 B2 | 8/2012 | Osorio et al. |
| 8,608,802 B2 | 12/2013 | Bagga et al. |
| 8,617,166 B2 | 12/2013 | Hanson et al. |
| 8,617,176 B2 | 12/2013 | Lizardi et al. |
| 8,636,745 B2 | 1/2014 | Almutairi et al. |
| 8,801,800 B2 | 8/2014 | Bagga et al. |
| 8,821,504 B2 | 9/2014 | Sharkey et al. |
| 8,864,768 B2 | 10/2014 | Hanson et al. |
| 8,906,032 B2 | 12/2014 | Hanson et al. |
| 8,951,261 B2 | 2/2015 | Sharkey et al. |
| 9,033,987 B2 | 5/2015 | Hanson et al. |
| 9,119,721 B2 | 9/2015 | Sharkey et al. |
| 9,259,257 B2 | 2/2016 | Bagga et al. |
| 9,271,835 B2 | 3/2016 | Bagga |
| 9,351,746 B2 | 5/2016 | Hanson et al. |
| 9,351,835 B2 | 5/2016 | Sharkey et al. |
| 9,386,996 B2 | 7/2016 | Hanson et al. |
| 9,439,765 B2 | 9/2016 | Bagga et al. |
| 9,717,544 B2 | 8/2017 | Sharkey et al. |
| 9,730,744 B2 | 8/2017 | Sharkey et al. |
| 10,271,883 B2 | 4/2019 | Sharkey et al. |
| 2002/0029084 A1 | 3/2002 | Paul et al. |
| 2002/0032447 A1 | 3/2002 | Weikel et al. |
| 2002/0049449 A1 | 4/2002 | Bhatnagar et al. |
| 2002/0133165 A1 | 9/2002 | Whittaker et al. |
| 2002/0151897 A1 | 10/2002 | Zirkie, Jr. |
| 2003/0009235 A1 | 1/2003 | Manrique et al. |
| 2003/0097135 A1 | 5/2003 | Penenberg |
| 2003/0105468 A1 | 6/2003 | Gorek |
| 2003/0120344 A1 | 6/2003 | Michelson |
| 2003/0138473 A1 | 7/2003 | Koblish et al. |
| 2003/0220651 A1 | 11/2003 | Pusnik et al. |
| 2003/0225456 A1 | 12/2003 | Ek |
| 2004/0002713 A1 | 1/2004 | Olson, Jr. et al. |
| 2004/0002759 A1 | 1/2004 | Ferree |
| 2004/0010261 A1 | 1/2004 | Hoag et al. |
| 2004/0106925 A1 | 6/2004 | Culbert |
| 2004/0127987 A1 | 7/2004 | Evans et al. |
| 2004/0167538 A1 | 8/2004 | Gerber et al. |
| 2004/0220583 A1 | 11/2004 | Pieczynski, II et al. |
| 2005/0075641 A1 | 4/2005 | Singhatat et al. |
| 2005/0119219 A1 | 6/2005 | Bellini et al. |
| 2005/0119753 A1 | 6/2005 | McGahan et al. |
| 2005/0149022 A1 | 7/2005 | Shaolian et al. |
| 2005/0159812 A1 | 7/2005 | Dinger, III et al. |
| 2005/0177171 A1 | 8/2005 | Wetzler et al. |
| 2005/0182418 A1 | 8/2005 | Boyd et al. |
| 2005/0203622 A1 | 9/2005 | Steiner et al. |
| 2005/0203623 A1 | 9/2005 | Steiner et al. |
| 2005/0256527 A1 | 11/2005 | Delfosse et al. |
| 2005/0267584 A1 | 12/2005 | Burdulis, Jr. et al. |
| 2005/0288795 A1 | 12/2005 | Bagga et al. |
| 2006/0052791 A1 | 3/2006 | Hagen et al. |
| 2006/0064164 A1 | 3/2006 | Thelen et al. |
| 2006/0084986 A1 | 4/2006 | Grinberg et al. |
| 2006/0247642 A1 | 11/2006 | Stone et al. |
| 2006/0271059 A1 | 11/2006 | Reay-Young et al. |
| 2007/0055280 A1 | 3/2007 | Osorio et al. |
| 2007/0093834 A1 | 4/2007 | Stevens et al. |
| 2007/0100462 A1 | 5/2007 | Lang et al. |
| 2007/0127987 A1 | 6/2007 | Altenbuchner |
| 2007/0225813 A1 | 9/2007 | Haines |
| 2007/0276370 A1 | 11/2007 | Altarac et al. |
| 2007/0282346 A1 | 12/2007 | Scribner et al. |
| 2008/0027434 A1 | 1/2008 | Zucherman et al. |
| 2008/0039857 A1 | 2/2008 | Giersch et al. |
| 2008/0039866 A1 | 2/2008 | Stetz et al. |
| 2008/0077251 A1 | 3/2008 | Chen et al. |
| 2008/0103506 A1 | 5/2008 | Volpi et al. |
| 2008/0195115 A1 | 8/2008 | Oren et al. |
| 2008/0243127 A1 | 10/2008 | Lang et al. |
| 2008/0262500 A1 | 10/2008 | Collazo |
| 2008/0281331 A1 | 11/2008 | Fritzinger et al. |
| 2008/0288006 A1 | 11/2008 | Brannon |
| 2008/0306490 A1 | 12/2008 | Lakin et al. |
| 2009/0062797 A1 | 3/2009 | Huebner et al. |
| 2009/0069901 A1 | 3/2009 | Truncale et al. |
| 2009/0093813 A1 | 4/2009 | Elghazaly |
| 2009/0204158 A1 | 8/2009 | Sweeney |
| 2010/0015202 A1 | 1/2010 | Semler et al. |
| 2010/0022952 A1 | 1/2010 | Solomon et al. |
| 2010/0076503 A1 | 3/2010 | Beyar et al. |
| 2010/0145451 A1 | 6/2010 | Dee |
| 2010/0160970 A1 | 6/2010 | Sevrain |

(56) References Cited

U.S. PATENT DOCUMENTS

| | | |
|---|---|---|
| 2010/0179549 A1 | 7/2010 | Keller et al. |
| 2010/0274254 A1 | 10/2010 | Boileau et al. |
| 2011/0125156 A1 | 5/2011 | Sharkey et al. |
| 2011/0125157 A1 | 5/2011 | Sharkey et al. |
| 2011/0125159 A1 | 5/2011 | Hanson et al. |
| 2011/0125160 A1 | 5/2011 | Bagga et al. |
| 2011/0125200 A1 | 5/2011 | Hanson et al. |
| 2011/0125201 A1 | 5/2011 | Hanson et al. |
| 2011/0125264 A1 | 5/2011 | Bagga et al. |
| 2011/0125265 A1 | 5/2011 | Bagga et al. |
| 2011/0125272 A1 | 5/2011 | Bagga et al. |
| 2014/0074103 A1 | 3/2014 | Mandeen et al. |
| 2014/0107781 A1 | 4/2014 | Bagga et al. |
| 2014/0114369 A1 | 4/2014 | Hanson et al. |
| 2014/0350683 A1 | 11/2014 | Sharkey et al. |
| 2014/0350685 A1 | 11/2014 | Bagga et al. |
| 2015/0025589 A1 | 1/2015 | Hanson et al. |
| 2015/0150616 A1 | 6/2015 | Sharkey et al. |
| 2015/0230807 A1 | 8/2015 | Hanson et al. |
| 2015/0257886 A1 | 9/2015 | Sharkey et al. |
| 2016/0270834 A1 | 9/2016 | Sharkey et al. |
| 2017/0258505 A1 | 9/2017 | Sharkey et al. |

FOREIGN PATENT DOCUMENTS

| | | |
|---|---|---|
| CN | 101460105 A | 6/2009 |
| CN | 102770067 A | 11/2012 |
| CN | 102781348 A | 11/2012 |
| CN | 102740784 B | 9/2015 |
| EP | 0327249 A2 | 8/1989 |
| EP | 0682916 A2 | 11/1995 |
| EP | 2501303 A1 | 9/2012 |
| EP | 2501306 A1 | 9/2012 |
| EP | 2501314 A1 | 9/2012 |
| EP | 2501342 A1 | 9/2012 |
| EP | 2501314 B1 | 4/2019 |
| FR | 2726458 A1 | 5/1996 |
| GB | 634460 A | 3/1950 |
| WO | WO-8903695 A1 | 5/1989 |
| WO | WO-9519141 A2 | 7/1995 |
| WO | WO-03084412 A1 | 10/2003 |
| WO | WO-2005079881 A1 | 9/2005 |
| WO | WO-2008155772 A1 | 12/2008 |
| WO | WO-2011063240 A1 | 5/2011 |
| WO | WO-2011063250 A1 | 5/2011 |
| WO | WO-2011063257 A1 | 5/2011 |
| WO | WO-2011063267 A1 | 5/2011 |
| WO | WO-2011063279 A1 | 5/2011 |
| WO | WO-2011063281 A1 | 5/2011 |

OTHER PUBLICATIONS

"European Application Serial No. 10832285.0, Response filed Mar. 5, 2018 to Extended European Search Report dated Aug. 16, 2017", 9 pgs.

"U.S. Appl. No. 12/950,061, Final Office Action dated Jul. 15, 2013", 7 pgs.

"U.S. Appl. No. 12/950,061, Non Final Office Action dated Feb. 7, 2013", 7 pgs.

"U.S. Appl. No. 12/950,061, Notice of Allowance dated Oct. 1, 2013", 6 pgs.

"U.S. Appl. No. 12/950,061, Preliminary Amendment dated Feb. 8, 2011", 3 pgs.

"U.S. Appl. No. 12/950,061, Response filed Jun. 7, 2013 to Non Final Office Action dated Feb. 7, 2013", 14 pgs.

"U.S. Appl. No. 12/950,061, Response filed Sep. 16, 2013 to Final Office Action dated Jul. 15, 2013", 13 pgs.

"U.S. Appl. No. 12/950,097, Final Office Action dated Dec. 10, 2013", 6 pgs.

"U.S. Appl. No. 12/950,097, Non Final Office Action dated Feb. 15, 2013", 8 pgs.

"U.S. Appl. No. 12/950,097, Non Final Office Action dated Aug. 6, 2013", 6 pgs.

"U.S. Appl. No. 12/950,097, Notice of Allowance dated Apr. 2, 2014", 5 pgs.

"U.S. Appl. No. 12/950,097, Notice of Allowance dated Jul. 9, 2014", 5 pgs.

"U.S. Appl. No. 12/950,097, Preliminary Amendment dated Feb. 7, 2011", 3 pgs.

"U.S. Appl. No. 12/950,097, Response filed Mar. 10, 2014 to Final Office Action dated Dec. 10, 2013", 13 pgs.

"U.S. Appl. No. 12/950,097, Response filed Jun. 17, 2013 to Non Final Office Action dated Feb. 15, 2013", 15 pgs.

"U.S. Appl. No. 12/950,097, Response filed Nov. 6, 2013 to Non Final Office Action dated Aug. 6, 2013", 14 pgs.

"U.S. Appl. No. 12/950,114, Final Office Action dated Jul. 15, 2013", 6 pgs.

"U.S. Appl. No. 12/950,114, Non Final Office Action dated Feb. 6, 2014", 6 pgs.

"U.S. Appl. No. 12/950,114, Non Final Office Action dated Mar. 7, 2013", 6 pgs.

"U.S. Appl. No. 12/950,114, Notice of Allowance dated Jun. 16, 2014", 5 pgs.

"U.S. Appl. No. 12/950,114, Preliminary Amendment dated Feb. 8, 2011", 3 pgs.

"U.S. Appl. No. 12/950,114, Response filed May 6, 2014 to Non-Final Office Action dated Feb. 6, 2014", 7 pgs.

"U.S. Appl. No. 12/950,114, Response filed Jun. 7, 2013 to Non Final Office Action dated Mar. 7, 2013", 8 pgs.

"U.S. Appl. No. 12/950,114, Response filed Sep. 16, 2013 to Final Office Action dated Jul. 15, 2013", 8 pgs.

"U.S. Appl. No. 12/950,154, Examiner Interview Summary dated Aug. 14, 2014", 3 pgs.

"U.S. Appl. No. 12/950,154, Final Office Action dated Aug. 8, 2013", 7 pgs.

"U.S. Appl. No. 12/950,154, Non Final Office Action dated Feb. 25, 2014", 6 pgs.

"U.S. Appl. No. 12/950,154, Non Final Office Action dated Mar. 15, 2013", 8 pgs.

"U.S. Appl. No. 12/950,154, Notice of Allowance dated Oct. 10, 2014", 6 pgs.

"U.S. Appl. No. 12/950,154, Preliminary Amendment dated Feb. 7, 2011", 4 pgs.

"U.S. Appl. No. 12/950,154, Response filed Jun. 17, 2013 to Non Final Office Action dated Mar. 15, 2013", 15 pgs.

"U.S. Appl. No. 12/950,154, Response filed Aug. 25, 2014 to Non-Final Office Action dated Feb. 25, 2014", 18 pgs.

"U.S. Appl. No. 12/950,154, Response filed Oct. 8, 2013 to Final Office Action dated Aug. 8, 2013", 18 pgs.

"U.S. Appl. No. 12/950,183, Examiner Interview Summary dated Feb. 13, 2014", 3 pgs.

"U.S. Appl. No. 12/950,183, Final Office Action dated Oct. 30, 2012", 16 pgs.

"U.S. Appl. No. 12/950,183, Non Final Office Action dated May 29, 2012", 10 pgs.

"U.S. Appl. No. 12/950,183, Non Final Office Action dated Oct. 11, 2013", 12 pgs.

"U.S. Appl. No. 12/950,183, Notice of Allowance dated Feb. 19, 2014", 5 pgs.

"U.S. Appl. No. 12/950,183, Notice of Allowance dated Jun. 6, 2014", 7 pgs.

"U.S. Appl. No. 12/950,183, Preliminary Amendment dated Feb. 8, 2011", 4 pgs.

"U.S. Appl. No. 12/950,183, Response filed Jan. 13, 2014 to Non Final Office Action dated Oct. 11, 2013", 11 pgs.

"U.S. Appl. No. 12/950,183, Response filed Apr. 30, 2013 to Final Office Action dated Oct. 30, 2012", 11 pgs.

"U.S. Appl. No. 12/950,183, Response filed May 11, 2012 to Restriction Requirement dated Apr. 13, 2012", 2 pgs.

"U.S. Appl. No. 12/950,183, Response filed Aug. 28, 2012 to Non Final Office Action dated May 29, 2012", 10 pgs.

"U.S. Appl. No. 12/950,183, Restriction Requirement dated Apr. 13, 2012", 8 pgs.

"U.S. Appl. No. 12/950,183, Supplemental Amendment dated Feb. 7, 2014", 8 pgs.

(56) References Cited

OTHER PUBLICATIONS

"U.S. Appl. No. 12/950,230, Examiner Interview Summary dated Nov. 12, 2014", 3 pgs.
"U.S. Appl. No. 12/950,230, Final Office Action dated Jan. 11, 2013", 10 pgs.
"U.S. Appl. No. 12/950,230, Final Office Action dated Jan. 13, 2015", 10 pgs.
"U.S. Appl. No. 12/950,230, Non Final Office Action dated Apr. 15, 2015", 10 pgs.
"U.S. Appl. No. 12/950,230, Non Final Office Action dated Jul. 17, 2014", 10 pgs.
"U.S. Appl. No. 12/950,230, Non Final Office Action dated Aug. 2, 2012", 9 pgs.
"U.S. Appl. No. 12/950,230, Notice of Allowance dated Oct. 7, 2015", 5 pgs.
"U.S. Appl. No. 12/950,230, Preliminary Amendment dated Feb. 8, 2011", 3 pgs.
"U.S. Appl. No. 12/950,230, Response filed Mar. 24, 2015 to Final Office Action dated Jan. 13, 2015", 11 pgs.
"U.S. Appl. No. 12/950,230, Response filed Apr. 11, 2013 to Final Office Action dated Jan. 11, 2013", 10 pgs.
"U.S. Appl. No. 12/950,230, Response filed Jul. 15, 2015 to Non Final Office Action dated Apr. 15, 2015", 16 pgs.
"U.S. Appl. No. 12/950,230, Response filed Nov. 2, 2012 to Non Final Office Action dated Aug. 2, 2012", 8 pgs.
"U.S. Appl. No. 12/950,230, Response filed Nov. 17, 2014 to Non-Final Office Action dated Jul. 17, 2014", 15 pgs.
"U.S. Appl. No. 12/950,273, Advisory Action dated May 12, 2015", 3 pgs.
"U.S. Appl. No. 12/950,273, Final Office Action dated Feb. 4, 2015", 28 pgs.
"U.S. Appl. No. 12/950,273, Final Office Action dated Mar. 14, 2016", 13 pgs.
"U.S. Appl. No. 12/950,273, Final Office Action dated Nov. 6, 2012", 9 pgs.
"U.S. Appl. No. 12/950,273, Non Final Office Action dated Apr. 13, 2012", 15 pgs.
"U.S. Appl. No. 12/950,273, Non Final Office Action dated Apr. 25, 2014", 12 pgs.
"U.S. Appl. No. 12/950,273, Non Final Office Action dated Nov. 24, 2015", 10 pgs.
"U.S. Appl. No. 12/950,273, Preliminary Amendment dated Feb. 8, 2011", 3 pgs.
"U.S. Appl. No. 12/950,273, Response filed Mar. 6, 2013 to Final Office Action dated Nov. 6, 2012", 10 pgs.
"U.S. Appl. No. 12/950,273, Response filed May 4, 2015 to Final Office Action dated Feb. 4, 2015", 14 pgs.
"U.S. Appl. No. 12/950,273, Response filed Jun. 14, 2015 to Final Office Action dated Feb. 4, 2015", 14 pgs.
"U.S. Appl. No. 12/950,273, Response filed Jul. 12, 2012 to Non Final Office Action dated Apr. 13, 2012", 12 pgs.
"U.S. Appl. No. 12/950,273, Response filed Oct. 24, 2014 to Non-Final Office Action dated Apr. 25, 2014", 14 pgs.
"U.S. Appl. No. 12/950,273, Response filed Dec. 29, 2015 to Non Final Office Action dated Nov. 24, 2015", 11 pgs.
"U.S. Appl. No. 12/950,306, Final Office Action dated Nov. 26, 2012", 9 pgs.
"U.S. Appl. No. 12/950,306, Non Final Office Action dated Jun. 14, 2012", 11 pgs.
"U.S. Appl. No. 12/950,306, Notice of Allowance dated May 28, 2013", 9 pgs.
"U.S. Appl. No. 12/950,306, Notice of Allowance dated Aug. 13, 2013", 9 pgs.
"U.S. Appl. No. 12/950,306, Preliminary Amendment dated Feb. 8, 2011", 7 pgs.
"U.S. Appl. No. 12/950,306, Response filed Apr. 30, 2013 to Final Office Action dated Nov. 26, 2012", 15 pgs.
"U.S. Appl. No. 12/950,306, Response filed Sep. 13, 2012 to Non Final Office Action dated Jun. 14, 2012", 11 pgs.
"U.S. Appl. No. 12/950,355, Final Office Action dated Mar. 12, 2013", 15 pgs.
"U.S. Appl. No. 12/950,355, Non Final Office Action dated Jul. 29, 2014", 9 pgs.
"U.S. Appl. No. 12/950,355, Non Final Office Action dated Aug. 13, 2012", 16 pgs.
"U.S. Appl. No. 12/950,355, Notice of Allowance dated Dec. 9, 2014", 6 pgs.
"U.S. Appl. No. 12/950,355, Response filed Jan. 14, 2013 to Non Final Office Action dated Aug. 13, 2012", 17 pgs.
"U.S. Appl. No. 12/950,355, Response filed Jul. 12, 2013 to Final Office Action dated Mar. 12, 2013", 20 pgs.
"U.S. Appl. No. 12/950,355, Response filed Oct. 28, 2014 to Non-Final Office Action dated Jul. 29, 2014", 21 pgs.
"U.S. Appl. No. 14/109,368, Final Office Action dated Jul. 9, 2015", 10 pgs.
"U.S. Appl. No. 14/109,368, Non Final Office Action dated Mar. 11, 2015", 6 pgs.
"U.S. Appl. No. 14/109,368, Notice of Allowance dated Nov. 24, 2015", 10 pgs.
"U.S. Appl. No. 14/109,368, Response filed May 26, 2015 to Non-Final Office Action dated Mar. 11, 2015", 12 pgs.
"U.S. Appl. No. 14/109,368, Response filed Nov. 9, 2015 to Final Office Action dated Jul. 9, 2015", 17 pgs.
"U.S. Appl. No. 14/143,883, Non Final Office Action dated Aug. 4, 2014", 6 pgs.
"U.S. Appl. No. 14/143,883, Notice of Allowance dated Jan. 26, 2015", 6 pgs.
"U.S. Appl. No. 14/143,883, Response filed Dec. 4, 2014 to Non-Final Office Action dated Aug. 4, 2014", 9 pgs.
"U.S. Appl. No. 14/453,301, Final Office Action dated Mar. 28, 2016", 11 pgs.
"U.S. Appl. No. 14/453,301, Non Final Office Action dated Sep. 23, 2015", 17 pgs.
"U.S. Appl. No. 14/453,301, Notice of Allowance dated Jun. 17, 2016", 8 pgs.
"U.S. Appl. No. 14/453,301, Preliminary Amendment dated Oct. 6, 2014", 8 pgs.
"U.S. Appl. No. 14/453,301, Response filed May 31, 2016 to Final Office Action dated Mar. 28, 2016", 11 pgs.
"U.S. Appl. No. 14/453,301, Response filed Dec. 23, 2015 to Non Final Office Action dated Sep. 23, 2015", 15 pgs.
"U.S. Appl. No. 14/454,298, Notice of Allowance dated Mar. 17, 2015", 8 pgs.
"U.S. Appl. No. 14/454,298, Notice of Allowance dated Jul. 1, 2015", 6 pgs.
"U.S. Appl. No. 14/454,298, Preliminary Amendment dated Sep. 18, 2014", 7 pgs.
"U.S. Appl. No. 14/508,436, Non Final Office Action dated Sep. 11, 2015", 7 pgs.
"U.S. Appl. No. 14/508,436, Notice of Allowance dated Feb. 4, 2016", 5 pgs.
"U.S. Appl. No. 14/508,436, Preliminary Amendment dated Jan. 8, 2015", 7 pgs.
"U.S. Appl. No. 14/508,436, Response filed Dec. 11, 2015 to Non Final Office Action dated Sep. 11, 2015", 10 pgs.
"U.S. Appl. No. 14/617,058, Non Final Office Action dated Sep. 29, 2016", 8 pgs.
"U.S. Appl. No. 14/617,058, Notice of Allowance dated Mar. 27, 2017", 5 pgs.
"U.S. Appl. No. 14/617,058, Preliminary Amendment dated Feb. 18, 2015", 8 pgs.
"U.S. Appl. No. 14/617,058, Reponse filed Jul. 18, 2016 to Restriction Requirement dated May 18, 2016", 7 pgs.
"U.S. Appl. No. 14/617,058, Response filed Dec. 16, 2016 to Non Final Office Action dated Sep. 19, 2016", 14 pgs.
"U.S. Appl. No. 14/617,058, Restriction Requirement dated May 18, 2016", 5 pgs.
"U.S. Appl. No. 14/695,516, Non Final Office Action dated Dec. 18, 2015", 8 pgs.
"U.S. Appl. No. 14/695,516, Notice of Allowability dated May 25, 2016", 2 pgs.

(56) References Cited

OTHER PUBLICATIONS

"U.S. Appl. No. 14/695,516, Notice of Allowance dated Apr. 28, 2016", 5 pgs.
"U.S. Appl. No. 14/695,516, Preliminary Amendment dated May 27, 2015", 6 pgs.
"U.S. Appl. No. 14/695,516, Response filed Mar. 14, 2016 to Non-Final Office Action dated Dec. 18, 2015", 10 pgs.
"U.S. Appl. No. 14/724,160, Non Final Office Action dated Sep. 11, 2015", 5 pgs.
"U.S. Appl. No. 14/724,160, Notice of Allowance dated Feb. 4, 2016", 5 pgs.
"U.S. Appl. No. 14/724,160, Preliminary Amendment dated Jun. 17, 2015", 8 pgs.
"U.S. Appl. No. 14/724,160, Response filed Nov. 25, 2015 to Non Final Office Action dated Sep. 11, 2015", 8 pgs.
"U.S. Appl. No. 15/166,345, Non Final Office Action dated Oct. 21, 2016", 6 pgs.
"U.S. Appl. No. 15/166,345, Notice of Allowance dated Apr. 5, 2017", 5 pgs.
"U.S. Appl. No. 15/166,345, Preliminary Amendment dated Jun. 1, 2016", 7 pgs.
"U.S. Appl. No. 15/166,345, Response filed Dec. 15, 2016 to Non Final Office Action dated Oct. 21, 2016", 8 pgs.
"U.S. Appl. No. 15/606,714, Non Final Office Action dated Jun. 29, 2018", 7 pgs.
"U.S. Appl. No. 15/606,714, Notice of Allowance dated Nov. 19, 2018", 5 pgs.
"U.S. Appl. No. 15/606,714, Preliminary Amendment dated May 31, 2017", 10 pgs.
"U.S. Appl. No. 15/606,714, Response Filed Sep. 28, 2018 to Non-Final Office Action dated Jun. 29, 2018", 8 pgs.
"Australian Application Serial No. 2010321745, Office Action dated Jan. 12, 2015", 3 pgs.
"Australian Application Serial No. 2010321745, Response filed Apr. 24, 2015 to Office Action dated Jan. 12, 2015", 18 pgs.
"Australian Application Serial No. 2010321812, Office Action dated Jan. 12, 2015", 3 pgs.
"Australian Application Serial No. 2010321812, Response filed Apr. 24, 2015 to Office Action dated Jan. 12, 2015", 19 pgs.
"Chinese Application Serial No. 201080020717.2, Office Action dated Jan. 9, 2014", (W/English Translation), 11 pgs.
"Chinese Application Serial No. 201080052569.2 Response filed Nov. 7, 2014 to Non Final Office Action dated Jun. 14, 2014", (W/ English Translation), 12 pgs.
"Chinese Application Serial No. 201080052569.2, Office Action dated Jan. 28, 2015", (W/ English Translation), 5 pgs.
"Chinese Application Serial No. 201080052569.2, Office Action dated Apr. 25, 2014", (W/English Translation), 17 pgs.
"Chinese Application Serial No. 201080052569.2, Response filed Mar. 26, 2015 to Office Action dated Jan. 28, 2015", (W/ English Claims), 10 pgs.
"Chinese Application Serial No. 201080052578.1, Office Action dated Apr. 1, 2014", (W/ English Translation), 11 pgs.
"Chinese Application Serial No. 201080052578.1, Office Action dated Dec. 17, 2014", (W/ English Translation), 4 pgs.
"Chinese Application Serial No. 201080052578.1, Response filed Jan. 22, 2015 to Office Action dated Dec. 17, 2014", (W/ English Translation), 8 pgs.
"Chinese Application Serial No. 201080052578.1, Response filed Aug. 12, 2014 to Office Action dated Apr. 1, 2014", (W/ English Claims), 13 pgs.
"Chinese Application Serial No. 201080052580.9, Office Action dated Apr. 3, 2014", w/English Translation, 18 pgs.
"Chinese Application Serial No. 201080052580.9, Office Action dated Nov. 25, 2014", (W/ English Translation), 18 pgs.
"Chinese Application Serial No. 201080052580.9, Response filed Aug. 14, 2014 to Office Action dated Apr. 3, 2014", (W/ English Claims), 12 pgs.
"Chinese Application Serial No. 201080052583.2, Office Action dated Mar. 14, 2014", (W//English Translation), 9 pgs.
"Chinese Application Serial No. 201080052583.2, Office Action dated Dec. 24, 2014", (W/English Translation), 4 pgs.
"Chinese Application Serial No. 201080052583.2, Response filed Sep. 26, 2014 to Office Action dated Mar. 14, 2014", (W/ English Translation of Claims), 10 pgs.
"European Application Serial No. 10832259.5, Extended European Search Report dated Oct. 24, 2017", 10 pgs.
"European Application Serial No. 10832277.7, Extended European Search Report dated Apr. 5, 2017", 9 pgs.
"European Application Serial No. 10832277.7, Office Action dated Jun. 27, 2012", 2 pgs.
"European Application Serial No. 10832277.7, Response filed Oct. 12, 2017 to Extended European Search Report dated Apr. 5, 2017", 21pgs.
"European Application Serial No. 10832285.0, Extended European Search Report dated Aug. 16, 2017", 11 pgs.
"European Application Serial No. 10832285.0, Office Action dated Jun. 27, 2012", 2 pgs.
"European Application Serial No. 10832292.6, Communication Pursuant to Article 94(3) EPC dated Sep. 18, 2018", 4 pgs.
"European Application Serial No. 10832292.6, Extended European Search Report dated Apr. 28, 2017", 8 pgs.
"European Application Serial No. 10832292.6, Response filed Jul. 21, 2017 to Extended European Search Report dated Apr. 28, 2017", 9 pgs.
"European Application Serial No. 10832293.4, Communication Pursuant to Article 94(3) EPC dated Oct. 10, 2018", 5 pgs.
"European Application Serial No. 10832293.4, Extended European Search Report dated Apr. 12, 2017", 10 pgs.
"European Application Serial No. 10832293.4, Response filed Oct. 24, 2017 to Extended European Search Report dated Apr. 12, 2017", 20 pgs.
"International Application Serial No. PCT/US2010/057426, International Preliminary Report on Patentability dated May 22, 2012", 9 pgs.
"International Application Serial No. PCT/US2010/057426, International Search Report and Written Opinion dated Jan. 24, 2011", 10 pgs.
"International Application Serial No. PCT/US2010/057440, International Preliminary Report on Patentability dated May 22, 2012", 7 pgs.
"International Application Serial No. PCT/US2010/057440, International Search Report and Written Opinion dated Feb. 7, 2011", 8 pgs.
"International Application Serial No. PCT/US2010/057456, International Preliminary Report on Patentability dated May 22, 2012", 6 pgs.
"International Application Serial No. PCT/US2010/057456, International Search Report and Written Opinion dated Jan. 14, 2011", 7 pgs.
"International Application Serial No. PCT/US2010/057471, International Preliminary Report on Patentability dated May 31, 2012", 7 pgs.
"International Application Serial No. PCT/US2010/057471, International Search Report dated Jan. 18, 2011", 2 pgs.
"International Application Serial No. PCT/US2010/057471, Written Opinion dated Jan. 18, 2011", 5 ogs.
"International Application Serial No. PCT/US2010/057475, International Preliminary Report on Patentability dated May 22, 2012", 6 pgs.
"International Application Serial No. PCT/US2010/057475, International Search Report dated Jan. 18, 2011", 8 pgs.
"International Application Serial No. PCT/US2010/057475, Written Opinion dated Jan. 18, 2011", 5 pgs.
"International Application Serial No. PCT/US2010/057483, International Preliminary Report on Patentability dated May 22, 2012", 6 pgs.
"International Application Serial No. PCT/US2010/057483, International Search Report and Written Opinion dated Feb. 2, 2011", 7 pgs.
"International Application Serial No. PCT/US2010/057498, International Preliminary Report on Patentability dated May 22, 2012", 5 pgs.

(56) References Cited

OTHER PUBLICATIONS

"International Application Serial No. PCT/US2010/057498, International Search Report dated Jan. 24, 2011", 2 pgs.
"International Application Serial No. PCT/US2010/057498, Written Opinion dated Jan. 24, 2011", 4 pgs.
"International Application Serial No. PCT/US2010/057500, International Preliminary Report on Patentability dated May 31, 2012", 8 pgs.
"International Application Serial No. PCT/US2010/057500, International Search Report dated Jan. 27, 2011", 2 pgs.
"International Application Serial No. PCT/US2010/057500, Written Opinion dated Jan. 27, 2011", 6 pgs.
"Riddle Memorial Hospital, Medial, PA 19063 Operative Report. Surgeon: Peter F Sharkey M.D.", Right Knee, Medial tibial plateau; A cannulated bone biopsy needle was placed into the bone under fluoroscopic guidance;, Implant used: Stryker Orthopedics Hydroset (Bone Substitute Material); Surgeon also expressed difficulty in injecting the bone substitute, (May 12, 2008), 2 pgs.
"SPU Operative Report. Surgen: Steven B Cohen, M.D.", Treatment of the central medial tibial plateau; A guide pin was inserted into the medial tibial plateau;, An endo button drill bit was used to expand the drill hole; One cubic centimeter (cc) of cement was inserted into the bone; A second drill hole was made from below, and a second cc was inserted into the bone., (Nov. 10, 2008), 4 pgs.
"SPU Operative Report: Surgen Steven B Cohen, M.D.", An Anterior Cruciate Ligament (ACL) portal-creation device was repurposed for this surgery; The tibial probe was placed on the medial femoral condyle, with the tunnel guide secured proximally on the thigh;, The surgeon expressed difficulty in positioning and stabilizing the guide; A cannulated pin was placed through the tunnel guide and placed distally into the medial femoral condyle; No implant was injected into the bone., (Oct. 27, 2008), 4 pgs.
"U.S. Appl. No. 15/606,714, Corrected Notice of Allowability dated Mar. 29, 2019", 2 pgs.
"U.S. Appl. No. 15/606,714, Corrected Notice of Allowability dated Dec. 31, 2018", 2 pgs.
"European Application Serial No. 10832259.5, Communication Pursuant to Article 94(3) EPC dated Aug. 1, 2019", 5 pgs.
"European Application Serial No. 10832259.5, Response filed Nov. 29, 2019 to Communication Pursuant to Article 94(3) EPC dated Aug. 1, 2019", 6 pgs.
"European Application Serial No. 10832292.6, Response filed Jan. 7, 2019 to Communication Pursuant to Article 94(3) EPC dated Sep. 18, 2018", 12 pgs.
"European Application Serial No. 10832293.4, Response Filed Jan. 24, 2019 to Communication Pursuant to Article 94(3) EPC dated Oct. 10, 2018", 24 pgs.

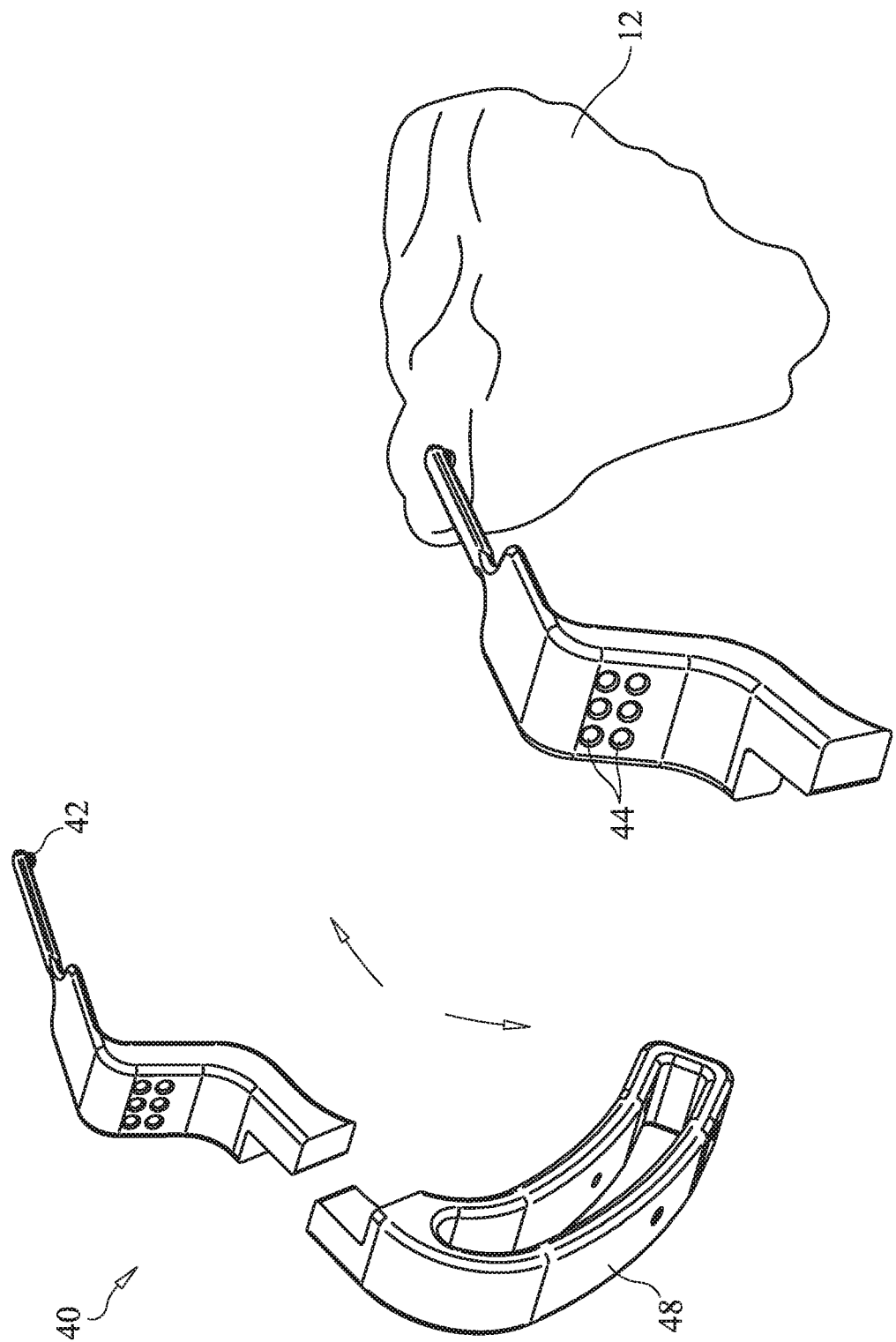

METHOD FOR TREATING JOINT PAIN AND ASSOCIATED INSTRUMENTS

CROSS-REFERENCE TO RELATED APPLICATIONS

This application is a continuation of U.S. patent application Ser. No. 15/606,714, filed May 26, 2017, which is a continuation of U.S. patent application Ser. No. 15/166,345, filed May 27, 2016, now issued as U.S. Pat. No. 9,730,744, which is a continuation of U.S. patent application Ser. No. 14/724,160, filed May 28, 2015, now issued as U.S. Pat. No. 9,351,835, which is a continuation of U.S. patent application Ser. No. 14/454,298, filed Aug. 7, 2014, now issued as U.S. Pat. No. 9,119,721, which is a continuation of U.S. patent application Ser. No. 12/950,097 filed Nov. 19, 2010, now issued as U.S. Pat. No. 8,821,504, which claims priority to U.S. Provisional No. 61/263,170 filed Nov. 20, 2009, and entitled "METHOD FOR TREATING JOINT PAIN AND ASSOCIATED INSTRUMENTS," which are herein incorporated by reference in their entirety.

This application also relates to co-owned U.S. patent application Ser. No. 12/950,355, filed Nov. 19, 2010, now U.S. Pat. No. 8,951,261, and entitled "SUBCHONDRAL TREATMENT OF JOINT PAIN," the content of which is herein incorporated in its entirety by reference.

FIELD

Embodiments of the present invention relate to devices, instruments, and associated methods for treating joint pain, and more particularly, knee pain.

BACKGROUND

Knee arthritis affects millions of people and the pain associated with this disease can be disabling. Patients who initially present with painful knee arthritis are usually treated non-surgically. Non-surgical treatments are modestly effective at temporarily relieving pain, but are not risk free. Pharmacologic intervention (i.e., non-steroidal anti-inflammatory drugs) has been reported to be associated with significant complications, such as gastric ulcers, strokes and heart attacks. A steroid or viscosupplement injection may lead to infection. Steroid injections may also have systemic effects, such as increased blood sugar and hypertension. Generally speaking, non-surgical interventions are most efficacious for early arthritic disease and do not prevent disease progression.

When non-surgical treatment proves ineffective, surgical intervention is often recommended. Arthroscopic surgery has been shown to have limited effectiveness and has a small role in the management of knee arthritis. More invasive surgical approaches such as high tibial osteotomy and partial or complete knee replacement predictably relieve pain. These major operations, however, are also potentially associated with significant morbidity and occasional mortality. These risks, along with the limited durability of implantable devices, cause patients and physicians to defer surgery until the symptoms become unbearable.

Some research has determined that glutamate transporters and receptors are highly expressed in subchondral proximal tibial bone in patients with osteoarthritis. The degree of expression of these transporters and receptors is directly proportional to the severity of the disease. Further, the increased expression occurs in the subchondral bone adjacent to the arthritic lesion. Thus, subchondral bone is likely an important source of pain management of osteoarthritis. See, "Expression of Glutamate Receptors and Transporters in Human Subchondral Bone in Osteoarthritis" by Christopher Wilson (Oct. 13, 2009).

Accordingly, it is desired to provide an effective, surgical treatment of osteoarthritis, and particularly knee arthritis pain. It is further desired that such surgical treatment be less invasive than high tibial osteotomy and partial or complete knee replacement.

SUMMARY

The present disclosure provides devices, instruments, and associated methods for treating joint pain. In particular, the joint is evaluated using magnetic resonance imaging to detect any anomalies in the subchondral bone. For example, using T2-weighted MRI images, bone marrow lesions or edemas can be identified, and using T1-weighted MRI images, associated regions of sclerotic bone adjacent to the bone marrow lesion can be identified. This condition may be the result of several factors, such as early arthritis, that results in an uneven concentration of loads in a joint. The uneven loads may cause a region of the bone to harden and become sclerotic, which can further aggravate the uneven load distribution. As a result, the sclerotic bone and uneven load may cause insufficiency fractures or fissures that appear as a bone marrow lesion or edema.

In one embodiment, the subchondral region of the bone is evaluated for the presence of one or more bone marrow lesions and a region of sclerotic bone. If these indications are found, then a SUBCHONDROPLASTY™ treatment may be employed to treat the joint pain. The method may involve introducing a bone void filler material at the site to address the bone marrow lesion or edema, and/or drilling and inserting an implant to address the sclerotic bone. This treatment may thus serve to reintegrate the bone and equalize load distribution to thereby relieve pain.

In one embodiment, a method for treating joint pain comprises: identifying a source of the pain of the joint based on an image of the joint, the image indicating the presence of a defect in the subchondral region of a bone of the joint; locating an insufficiency fracture in the subchondral region of the joint; mapping an access path to a location in the subchondral region where the insufficiency fracture resides, wherein the access path preserves an articular surface of the joint; and implanting in the bone, via the access path, a reinforcing member that stabilizes the insufficiency fracture.

In another embodiment, an instrument for guiding a tool to a target location in a bone adjacent to a joint comprises: a first portion having a first guide section configured to guide the tool to the target location; a reference probe extending from the first portion having a tip that indicates a selected landmark on the bone; and a handle portion coupled to the first portion and having a second guide section configured to guide a tool to the target location. The first guide section is configured to guide the tool at an angle substantially parallel to the reference probe, and the second guide section is configured to guide the tool at an angle acute to the reference probe.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIGS. 12-16 illustrate a method of treating a subchondral region of a bone based on another embodiment of the present invention.

DESCRIPTION OF THE EMBODIMENTS

Figure 1:
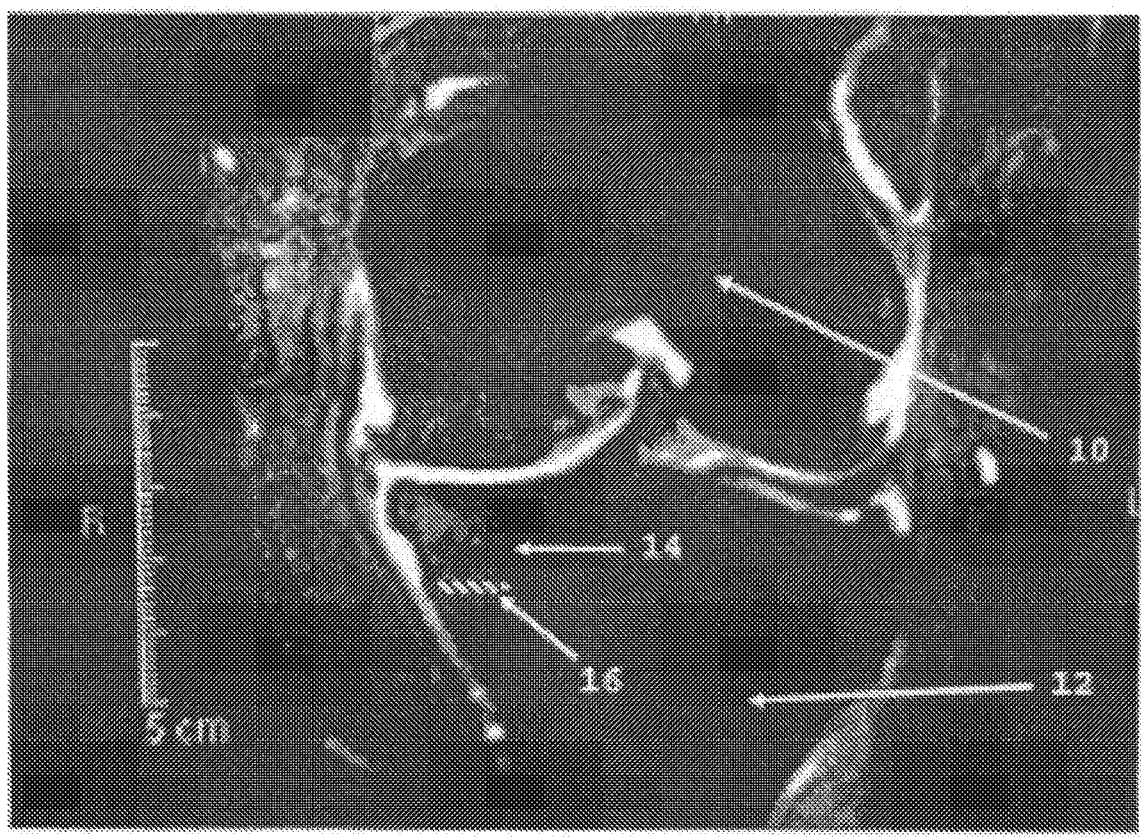
FIG. 1 is a magnetic resonance image (MRI) of an arthritic knee on which is overlaid a side view of an embodiment of the reinforcing member of the invention.

In general, the embodiments relate to devices, instruments and associated methods for treating joint pain in the subchondral region of the bone. One embodiment involves identifying defects in the subchondral region of a bone, such as a bone marrow lesion or edema adjacent to the joint, where sclerotic bone is also present, and then treating the defects such as by implanting an implant, such as a reinforcing member, in or adjacent to the abnormality or bone marrow lesion. Another treatment may involve the introduction of bone void material. In some embodiments, bone marrow lesions are considered an indicator of overstressed bone. In general, a bone marrow lesion may be any abnormal area or fracture in the bone. That is, any fracture non-union having a pathology indicating an amorphous structure with osseous and fibrous elements may be treatable by embodiments of the present invention.

Overstressed bone sustains more damage than repair and this often results in pain to a patient. Bone is continuously fatigued and damaged by everyday activity. However, bone is a living tissue that is capable of repairing itself. Certain pathological processes, such as loss of joint cartilage or joint deformation, can disturb the natural repair processes of healthy bone.

Embodiments of the invention may enhance the strength of bone and provide shielding to the subchondral region of the bone to prevent or minimize excessive stress using a subchondral surgical treatment marketed under the trademark SUBCHONDROPLASTY™. SUBCHONDROPLASTY™ treatment may be useful for treating joint pain, such as knee pain, where sclerotic bone and an associated anomaly or defect such as bone marrow lesion or edema is found. In some embodiments, bone marrow lesions or insufficiency fractures may be treated by SUBCHONDROPLASTY™ using an open reduction, internal fixation of the bone's abnormal area or area adjacent to the abnormality. In particular, in SUBCHONDROPLASTY™, the sclerotic bone may be treated using drilling and insertion of an implant. In addition, an associated bone marrow lesion or edema may be treated by injection of a bone void filler, such as a calcium phosphate cement (CPC).

Based on the implant and surgical method, a subchondral region of the bone may be treated and strengthened to restore its strength/repair equilibrium. In addition, strengthening the bone reduces, reverses and/or prevents the deformation of overstressed bone, which may relieve pain and slow arthritic disease progression within the underlying bone and adjacent meniscal tissues, such as cartilage.

In some embodiments, the invention provides an additional treatment option for patients suffering with arthritic pain, particularly in the knee. The method of the invention may be performed based on minor or outpatient surgery. Thus, the risk of complications is expected to be significantly less than with major arthritis surgery, such as more invasive procedures like high tibial osteotomy and partial or total knee replacement. In some embodiments, the implant and methods stabilize the defect in the subchondral (underlying) bone in order to prevent further biomechanical breakdown of the subchondral region of the bone and of the adjacent meniscal tissues, and alleviate the corresponding pain in the joint.

For example, the devices and methods of the present invention may promote integration of the bone marrow lesion with the surrounding bone. In other words, the implant and methods may serve to bridge the surrounding bone having one or more bone marrow lesions or bone insufficiency fractures. The surrounding region may even be dense sclerotic bone. In some embodiments, the implant may serve to redistribute the stress within the bone (especially in a weight bearing bone), and thus, may reduce pain. In other words, the implant may essentially dampen or prevent the force transmission that causes pain from the subchondral region of the bone. The implant is designed to have optimal stiffness and may be bioactive to facilitate the healing processes of the bone and integration of any abnormal areas, such as bone marrow lesions or insufficiency fractures, within the bone.

In a joint having a subchondral area of thinned or damaged bone, or an area absent of cartilage, there often exists nearby defects such as insufficiency fractures or fissures. Along with an insufficiency fracture there is often a region of dense sclerotic bone, possibly created by the concentration of joint forces at this localized region. It is believed that, over time, the joint forces acting on this dense sclerotic bone creates abnormal distribution of forces that lead to anomalies such as bone marrow lesions or edemas. The sclerotic bone region can be identified using T1-weighted MRI, while the bone marrow lesion or edema can often be identified using T2-weighted MRI.

As noted, embodiments of the present invention may be explained and illustrated with reference to treatment of a patient's knee, though it is understood that the devices, instruments and methods of the present invention may be applicable to other joints as well, such as the shoulder, hip and ankle. Referring now to FIG. 1, an arthritic human knee comprises a femur 10 and a tibia 12. Bone lesion 14 of tibia 12 presents as a focally increased signal in the marrow in an MRI of the knee. In certain embodiments, coronal spin-echo fat-saturated proton density, T1ρ proteoglycan and T2-weighted fat-saturated magnetic resonance images are preferred. In some embodiments, bone lesions, which are from 0 to 10 cm from the joint, 0 to 5 cm from the joint, or 0 to 1 cm from the joint are considered good candidates for treatment.

A bone marrow lesion 14 or other abnormality causing pain can be identified using magnetic resonance imaging (MRI), such as a T2-weighted MRI, but other identification means may be employed as well. For example, bone lesions can be identified using X-ray or Technetium-99 bone scans. In embodiments employing MRI, any MRI technology that reveals bone marrow lesions can be used, for example, open MRI, low field strength MRI, extremity MRI, whole body scanner MRI, and the like. In another embodiment, 3-dimensional imaging or image guidance technology may be employed to locate the lesion or defect. Such imaging technology would enable the lesion or defect to be located intraoperatively.

Various criteria may be employed for selecting an implant in accordance with principles of the present invention. For example, a reinforcing member 16 as an implant may be selected based on a grading system that indicates an extent of treatment for various types and sizes of bone marrow lesions or defects.

FIG. 1 shows just one example of how reinforcing member 16 could be implanted in bone lesion 14. Of course, the reinforcing member 16 may be implanted adjacent to the bone lesion 14. For example, the reinforcing member 16 can be implanted adjacent to a side of the bone lesion proximal to the joint and/or adjacent to a side of the bone lesion distal to the joint.

FIG. 1 shows one reinforcing member 16 implanted. Those skilled in the art will recognize that multiple reinforcing members can be implanted in and/or adjacent to a bone lesion according to other embodiments. In general, an implant that is 10 mm (or less) away from an outer surface of the bone lesion can be considered adjacent to that lesion. Adjacent reinforcing members can also be in contact with an outer surface of the bone lesion.

In general, the reinforcing member 16 serves to adequately distribute stresses placed on the bone. The reinforcing member 16 may be bioactive and configured to have an appropriate rigidity/flexibility and other characteristics, such as porous or non-porous coatings, as desired. In particular, the reinforcing member 16 may be sufficiently strong or stiff to make it capable of being implanted in bone and avoid stress concentration, for example, in the subchondral region of the bone. Accordingly, the reinforcing member 16 may have various dimensions and stiffness.

In some embodiments, the implant is implanted free of bonds to the bone. Thus, the reinforcing member is not, for example, glued, cemented, stapled, stitched, clamped or screwed to the bone. However, the implant may naturally or be configured to eventually bond to the bone via biological processes in situ.

In some embodiments, the reinforcing member 16 is implanted in the bone in or adjacent the bone lesion such that a proximal face faces the joint and a distal face faces away from the joint. In addition, the reinforcing member 16 may be selected or modified (e.g., cut, torn, etc.) such that a maximum dimension of the proximal face exceeds a maximum dimension of the bone lesion. It is also within the scope of the invention for the maximum dimension of the bone lesion to equal or exceed a maximum dimension of the proximal face. Thus, the reinforcing member 16 can be larger, smaller or the same size as the bone lesion.

The reinforcing member 16 can be implanted such that the proximal face is perpendicular to a longitudinal axis of the bone. In general, proximal and/or distal faces of the implant will be the primary load bearing surfaces in situ.

In certain embodiments, a syringe (optionally with a needle) can be used to inject a fluid into a bone so as to form the reinforcing member in situ. This step can be conducted with or without first creating an opening in the bone. The fluid is preferably a liquid, semi-solid, gel, hydrogel, dispersion or slurry. After injection, the fluid can remain fluid-like, or may cure to a more solid-like state. For example, the injected fluid can cross-link or polymerize from a liquid to form a semi-solid, gel or solid. Fluids that cure in situ can be self-curing or can cure in response to curing means, such as, e.g., radiation (e.g., UV light), heat (e.g., body temperature), moisture and/or a curing agent.

In other embodiments, the reinforcing member is solid in nature and may be rigid or malleable. In these embodiments, the surgeon creates a small opening in the vicinity of the bone lesion. Suitable surgical tools for this task include standard bone instruments (e.g., chisels, drills, etc.) and instruments, such as a guide/insertion instrument, designed for use in the method of the invention.

A surgeon can implant the reinforcing member 16 by studying a previously captured image of the bone marrow lesion 14 and manually estimating the location and boundaries of the bone lesion. Alternatively, a surgeon can be provided with additional guidance during surgery. For example, surgery can be conducted using real-time imaging, robotic devices, one or more braces that maintain the joint in a position consistent with captured images of the joint and/or labels, etc. Suitable labels include but are not limited to radioactive labels, such as Technetium-99 and other objects, such as fiducial markers.

Postoperatively, patients may be required to maintain partial weight bearing and use ambulatory aids. Depending upon the physician's discretion, full weight bearing may also be possible after surgery. Routine post intervention physical therapy may also be required. Patients may be treated according to routine post intervention care, observation and follow-up.

The reinforcing member 16 may have various forms and shapes to maximize its surface area and reduce stress of the bone when implanted. For example, the reinforcing member 16 may be in the form of a rod having a triangular profile, a rectangular profile, or a circular profile. Reinforcing member 16 may be planar, e.g., relatively long in two dimensions and relatively short in a third dimension. Planar reinforcing members in accordance with the invention can have a thickness which is ≤50% of the length and ≤50% of the width of a rectangular reinforcing member (or ≤50% of the diameter in the case of a circular reinforcing member or ≤50% of the height and ≤50% of the base in the case of a triangular reinforcing member).

In other embodiments, the reinforcing member 16 may have a wedge-shaped edge on at least one edge or a wedge or ramp shape when viewed from the side. A wedge-shaped edge may be adapted to facilitate inserting the reinforcing member 16 into the bone. Thus, the particular angle and other dimensions of the wedge may be dictated by factors that are known in the art. As a wedge-shaped implant, the reinforcing member 16 may be similar to standard surgical tools, such as osteotomes, or comprise blade plates or osteotomy staples. Further, the reinforcing member 16 may be an expandable device that can span the defect. In one embodiment, the reinforcing member 16 may be an expandable screw, such as an osseoscrew.

In other embodiments, the reinforcing member 16 may be in the form of a closed disc, an open disc, a screw-shaped device, or an elongated pin. In addition, the reinforcing member 16 may have a square profile, rectangular profile with rounded edges, or an I-beam profile. Alternatively, the reinforcing member 16 can be an injection cement diffuser. In some embodiments, the reinforcing member 16 may be approximately 3 mm thick.

In some embodiments, the reinforcing member 16 may be customized to the patient. For example, using 3-dimensional imaging technology, it may be desirable to provide an implant that matches precisely the anatomical site where the reinforcing member 16 is to be placed. This would ensure conformability and avoid a less than perfect match between the implant and the implantation site.

The reinforcing member 16 may be porous and/or fenestrated to allow for bone ingrowth. Reinforcing member 16 comprises a physiologically compatible material that has sufficient durability to reinforce the overstressed bone of the bone lesion and bear physiologic loads. Materials for the reinforcing member 16 can include metals, such as titanium, stainless steel, alloys of cobalt and chrome, tantalum, alloys of titanium and nickel and other superelastic metal alloys. Porous, titanium, titanium "foam", tantalum, trabecular metals, nanoceramics, porous nitinol, or other highly porous nanomaterials, and chrome cobalt may also be employed in the reinforcing member 16.

The reinforcing member 16 may comprise a functional coating, such as, hydroxyapatite plasma coating, titanium nitrate or bioactive glass. In addition, the reinforcing member 16 may undergo some form of surface treatment including acid etching, grit blast, or plasma spray. The reinforcing member may also comprise structural enhancements such as meshes, and include autograft. The member 16 may also be formed of, or include, porous metals like tantalum or ACTIPORE™.

Other embodiments comprise the use of bone, such as autografts, allografts, and artificial or synthetic bone substitutes. Certain embodiments comprise the use of polymeric materials. A combination of materials, such as a porous metal applied to a carbon fiber implant may be employed in the reinforcing member 16.

Reinforcing member 16 can be osteogenic, osteoconductive, and/or osteoinductive. Osteoconductive materials that may be used include but are not limited to collagen and the various forms of calcium phosphates including hydroxyapatite, tricalcium phosphate, and fluoroapatite. Suitable osteoinductive substances include but are not limited to bone morphogenetic proteins (e.g., rhBMP-2), demineralized bone matrix, transforming growth factors (e.g., TGF-beta), osteoblast cells, and various other organic species known to induce bone formation. Bone marrow, blood plasma, or morselized bone of the patient, or commercially available materials may also be used.

The reinforcing member 16 may be treated prior to implantation. For example, the reinforcing member 16 may be dipped or coated with bone conductive or bone inductive material. Osteoinductive materials, such as BMP, may be applied to, for example, by immersing the reinforcing member 16 in an aqueous solution of this material in a dilute suspension of type I collagen. Osteoinductive materials such as TGF-beta may be applied from a saline solution containing an effective concentration of TGF-beta, or may be carried in the resilient material. Of course, other biologics may be applied by any method known in the art.

The reinforcing member can be resorbable or non-resorbable. For example, the reinforcing member 16 may comprise PEEK, PGA, or PLA material. Electrical stimulation can also be applied to the bone to promote bone healing. The reinforcing member 16 may also be capable of imbibing bone stimulating material, such as porous nitinol, e.g., ACTIPORE™ or other form of porous coated titanium or periapatite coated titanium.

In some embodiments, implantation of the reinforcing member 16 may be achieved step-wise in multiple stages. For example, the reinforcing member 16 may be constructed to be implanted at an initial stage to establish primary fixation, then at a subsequent stage additional implantation or assembly can be performed to add increased pull-out strength and other reinforcing properties to the fully assembled reinforcing member 16.

Figure 2A:
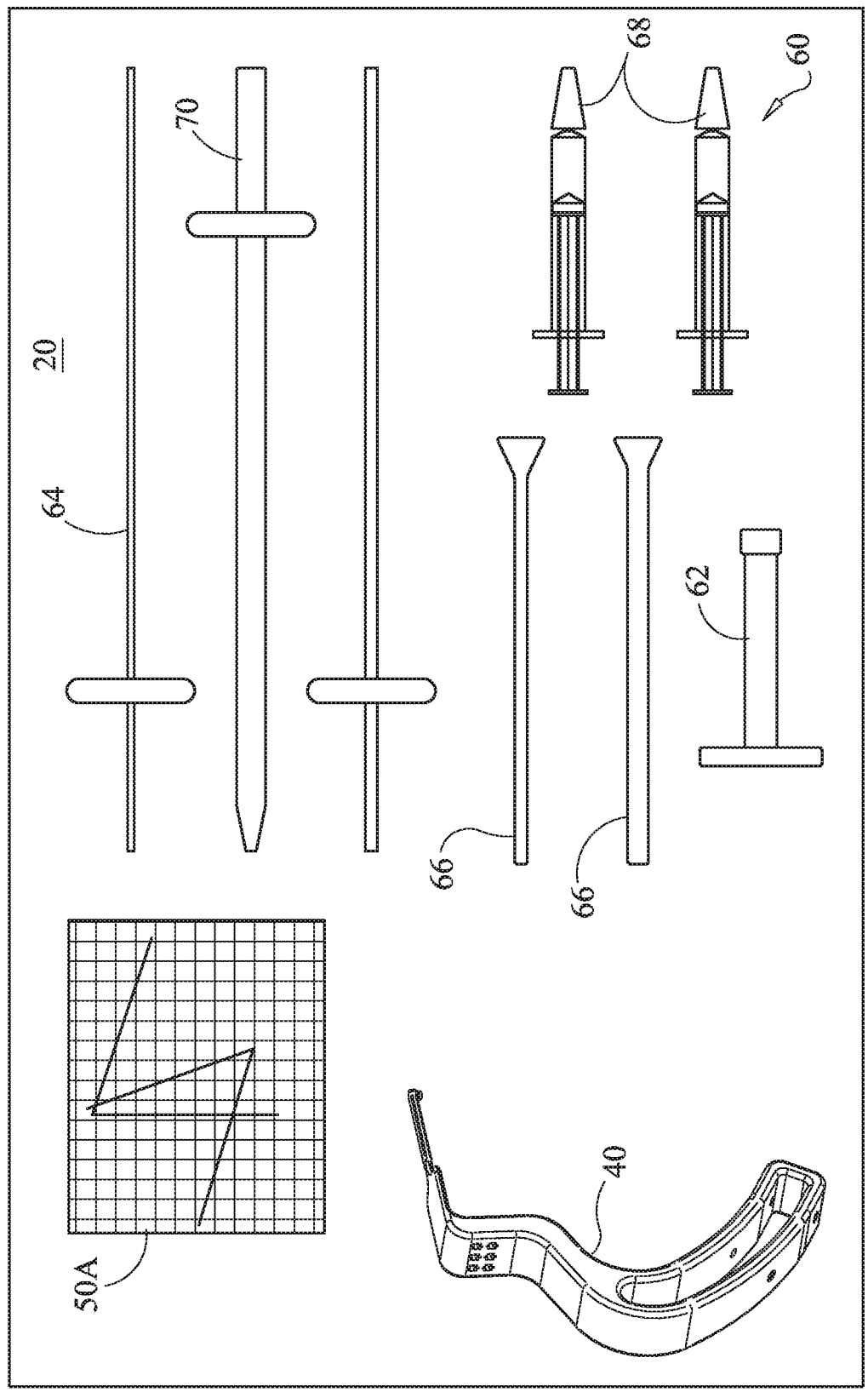
FIGS. 2A and 2B show exemplary SUBCHONDROPLASTY™ kits.
Figure 2B:
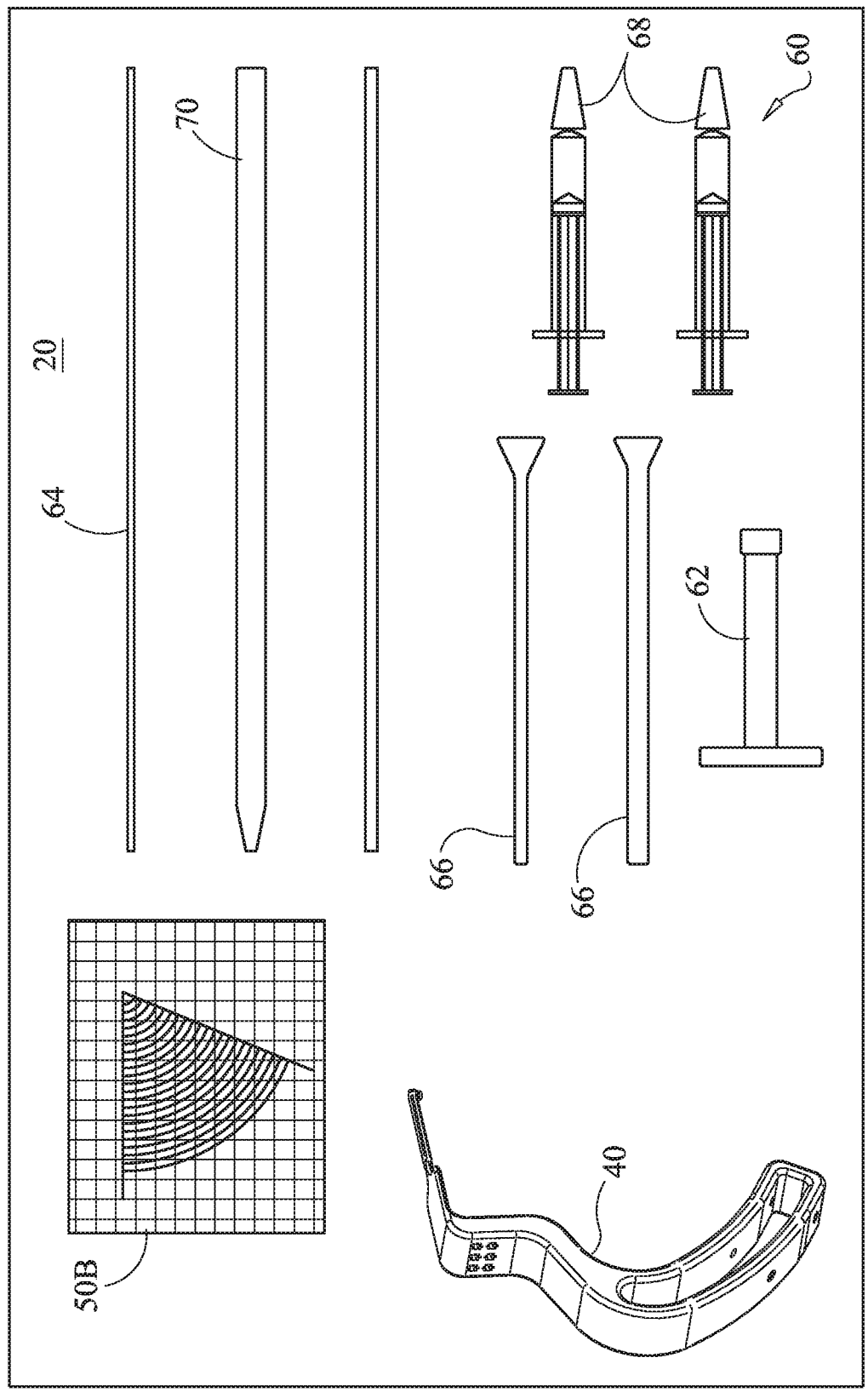

FIGS. 2A and 2B show exemplary SUBCHONDROPLASTY™ kits 20. These kits 20 are provided for facilitating the injection of bone void filler into subchondral insufficiency fractures in a subchondral surgical procedure that will be referred to under its marketed name as SUBCHONDROPLASTY™ or SCP™. As shown, the components of the kit may include, among other things, a SUBCHONDROPLASTY™ guide/insertion instrument 40, SCP™ templates 50A, 50B, and various tools 60 for assessment and/or drilling. For example, the tools 60 provided in kit 20 may include a volume assessment tool, a fixed bone portal 62, a Kirschner wire (or K-wire) 64, a bore creation device, several injection catheters 66 sized to match the bore creation device, several syringes 68, and a portal hole plug. In some embodiments, the kits 20 are provided to surgeon or medical facility prepackaged and sterile. In addition, some or all of the instruments and tools provided in the kit 20 may be reusable or disposable.

The kits 20 may also include a cavity creation device (not shown in FIGS. 2A and 2B). Cavity creation devices may include burrs, punches, reamers, rongeurs, tamps, drills 70, instruments with expandable components, such as balloons, stents or looped wires, instruments with a selectively angulatable or reconfigurable distal ends, and others known in the art.

As shown, in FIG. 2A, a first embodiment of the kit 20 can include an assortment of reinforcing members, such as reinforcing member 16, of various sizes and/or shapes appropriate for use with a variety of bone lesions. The kit 20 can also include instructions for use, e.g., printed on the container and/or on inserts within the container. The kit 20 can still further include a tool for adjusting the size of the reinforcing member 16, a hammer for driving the reinforcing member 16 into the bone and/or a bone filler to seal the open end of the channel in the bone in which the reinforcing member 16 resides. As noted, the kit 20 may be prepackaged and sterile with an assortment of reusable or disposable instruments and tools.

Suitable bone fillers include but are not limited to materials comprising beta-tricalcium phosphate (e.g., VITOSS, PROOSTEON 500R made by E-Interpore-Cross International), hydroxyapatite (e.g., OSTEOGRAF made by Ceramed Denta, Inc., Lakewood, Colo.), calcium carbonate, calcium sulfate (e.g., OSTEOSET and ALLOMATRIX made by Wright Medical Technology, Inc.), calcium phosphate (e.g., CALCIBON made by Merck & Co., Inc., Whitehouse Station, N.J. and NORIAN SRS made by Synthes-Strates, Switzerland), synthetic bone fillers (e.g., CORTOSS) and/or processed bone fillers (e.g., BIOOSS made by Geistlich Biomaterials, Inc., Switzerland). Other suitable materials may include hydrogels, PEEK (polyetheretherketone), carbon fiber, polycarbonate urethane (PCU), stem cells with and without matrices, collagen with and without matrices and carriers, pharmacotherapeutic with and without matrices and carriers, hyaluronic acid with and without matrices, in situ curable materials with and without anti-inflammatory agents, demineralized bone matrix, allograft, biocompatible metals, resorbable PCA, PGLA, and polyurethane, hydroxyapatite, calcium sulfate, BMP growth factor, TGF-β super family, MP52, TP508, bioactive glass, sodium alignate, AOC based carrier and active components (synthetic beeswax), and starch.

In some embodiments, the bone filler may be of a type that can expand upon insertion into the void. For example, the filler may be injectable at the defect site, whereupon it can fill up or expand into the void. And as with the reinforcing member 16, the bone void filler may also be implanted in a step-wise fashion such that an initial stage to establish primary fixation is followed with a subsequent stage of assembly that provides added strength and bone integration properties to the fully assembled bone void filler.

As shown in FIG. 2B, another embodiment of the kit 20 can include a fluid, a syringe for injecting the fluid into a bone and a container adapted to maintain the sterility of the contents of the container. As noted, the kit 20 may be prepackaged and sterile with an assortment of reusable or disposable instruments. This embodiment of the kit 20 can further comprise a needle and premeasured portions of ingredients in a plurality of separate vials. As with the first embodiment of the kit 20, this embodiment can optionally include instructions for use, e.g., printed on the container and/or on inserts within the container. The kit 20 can further include bone tools for providing a channel in the bone in which the fluid is injected and/or a bone filler to seal the open end of the channel in the bone in which the reinforcing member resides.

The kit 20 can further include curing agents (i.e., polymerizing agents, catalysts and/or cross linking agents) as separate ingredients to be added to the injected fluid. The kit 20 can include other curing means, such as a UV light source or other device for generating radiation. The fluid can be preloaded in the syringe for injection. In some embodiments, a multiple barrel syringe can be included for in situ mixing of ingredients that must be stored separately in different barrels of the syringe (e.g., monomers and polymerizing agent, or polymers and cross linking agent, etc.).

Figure 3A:
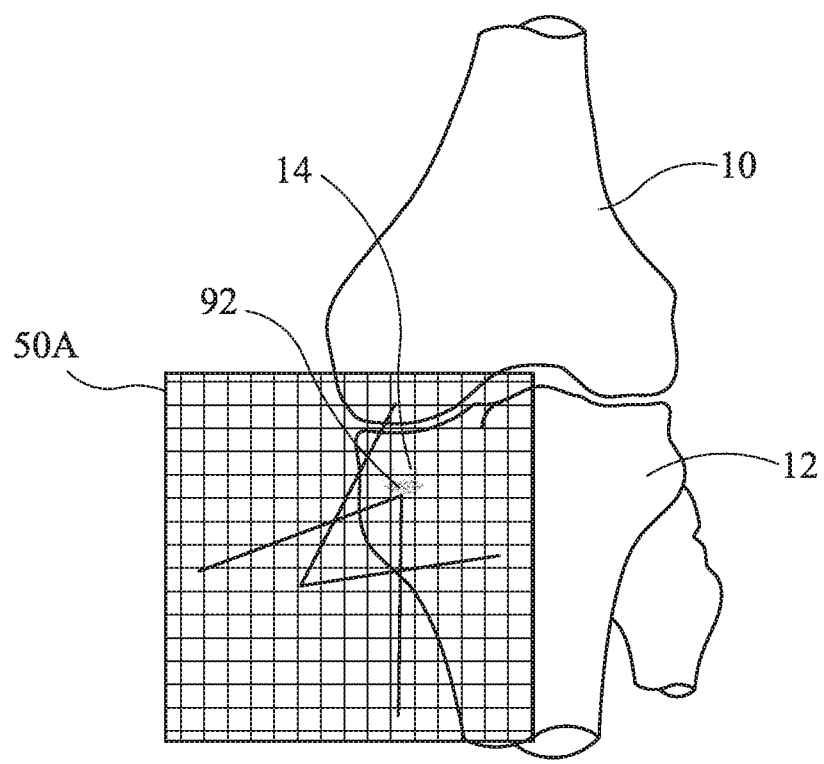
FIG. 3A shows a SUBCHONDROPLASTY™ template of the kit from FIG. 2A in use.
Figure 3B:
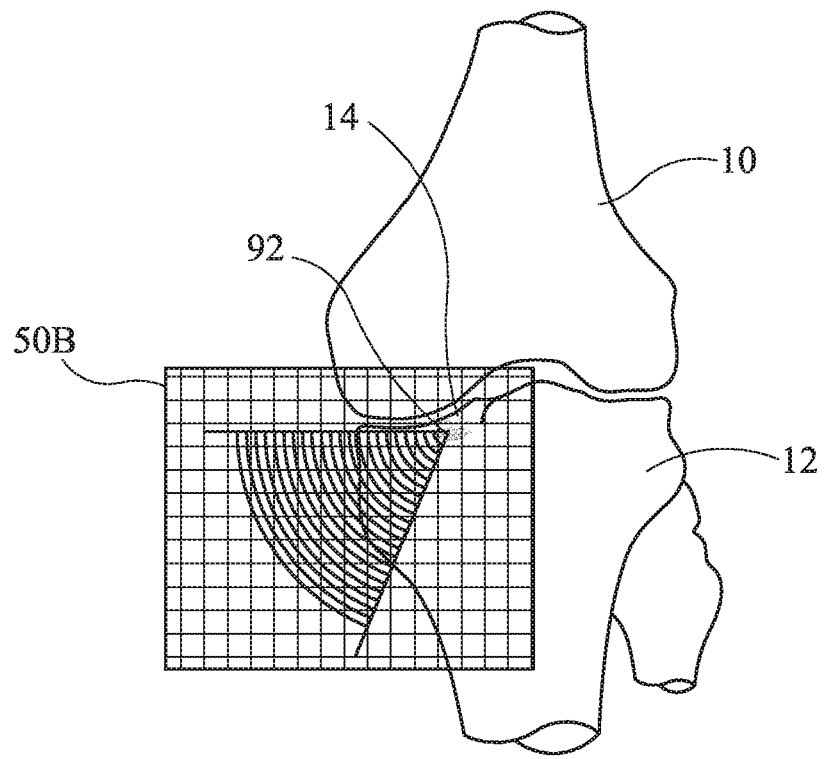
FIG. 3B shows a SUBCHONDROPLASTY™ template of the kit from FIG. 2B in use.

FIG. 3A shows a SUBCHONDROPLASTY™ template 50A of the kit 20 from FIG. 2A in use. FIG. 3B shows a SUBCHONDROPLASTY™ template 50B of the kit 20 from FIG. 2B in use. As part of the pre-operative planning process, medical imaging, such as an MRI illustrated in FIG. 1, is taken of the knee of a patient suffering from arthritic pain. For purposes of clarity, FIGS. 3A and 3B show the templates 50A, 50B overlaying a simplified illustration of a knee. A subchondral insufficiency fracture 92 associated with lesion 14 may then be identified and located on the MRI. The fracture size, volume and orientation are determined from the image, and based on the values, the recommended volume of bone void filler is determined from the volume assessment tool.

The SCP™ templates 50A and 50B, shown in FIGS. 3A and 3B, may be a transparent to indicate how a lesion can be treated. In use, for example, the templates 50A and 50B are placed over the MRI image to determine the placement of the SCP™ guide/insertion instrument 40, the appropriate location for a bone portal 62, and the resulting depth to the fracture.

Figure 4A:
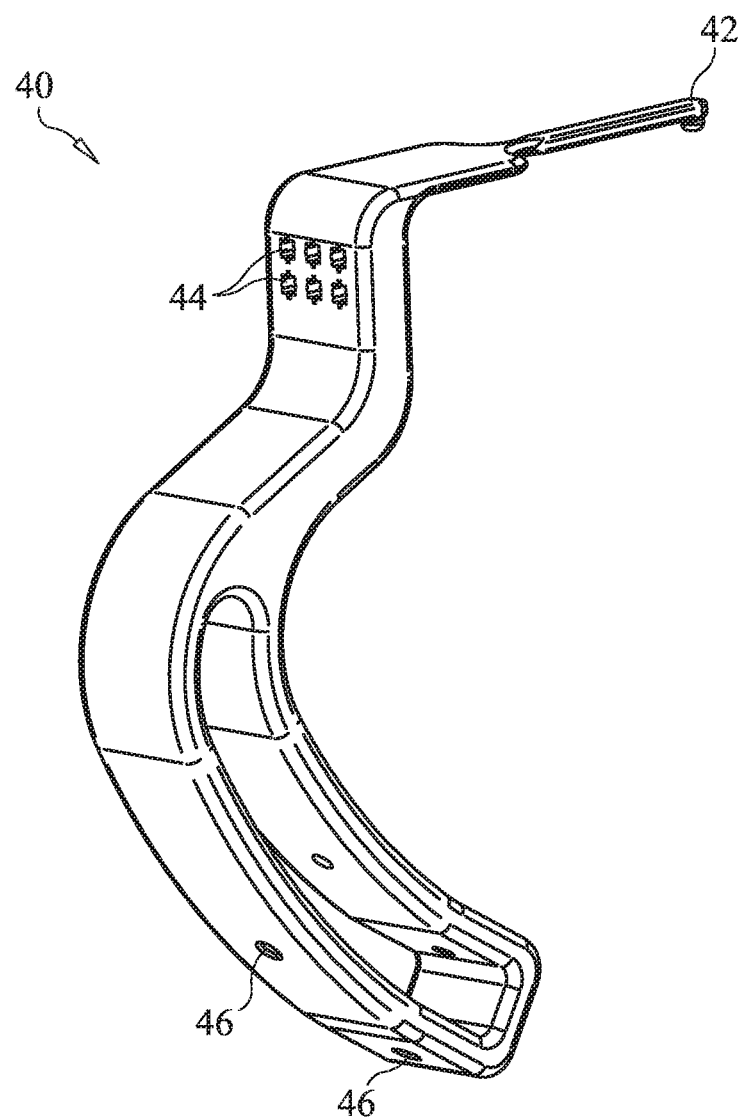
FIG. 4A shows an exemplary embodiment of the SUBCHONDROPLASTY™ guide/insertion tool or instrument.

FIG. 4A shows an exemplary embodiment of a SUBCHONDROPLASTY™ guide/insertion instrument 40. As shown, the guide/insertion instrument 40 may comprise an integrated cartilage reference 42, a parallel drill/implant guide 44, and angular drill guide/portal 46

The SCP™ guide/insertion instrument 40 is included in the kit 20 to aim the bone portal 62 and to set the depth stop of drilling for the surgeon. As shown, the SCP™ guide/insertion instrument 40 may comprise a curved body, a probe, and an optional adjustable arm (not shown). The curved body has a radius of curvature that provides for different angles of approach to the tip of the probe. The probe is attached to the curved body and may have a planar, rasped tip for contacting and gripping the articular surface of the knee joint without damaging the cartilage. The optional adjustable arm (not shown) may be connected to the curved body through a sliding arrangement such that the angle of the arm is adjustable with respect to the curved body.

Figure 4B:
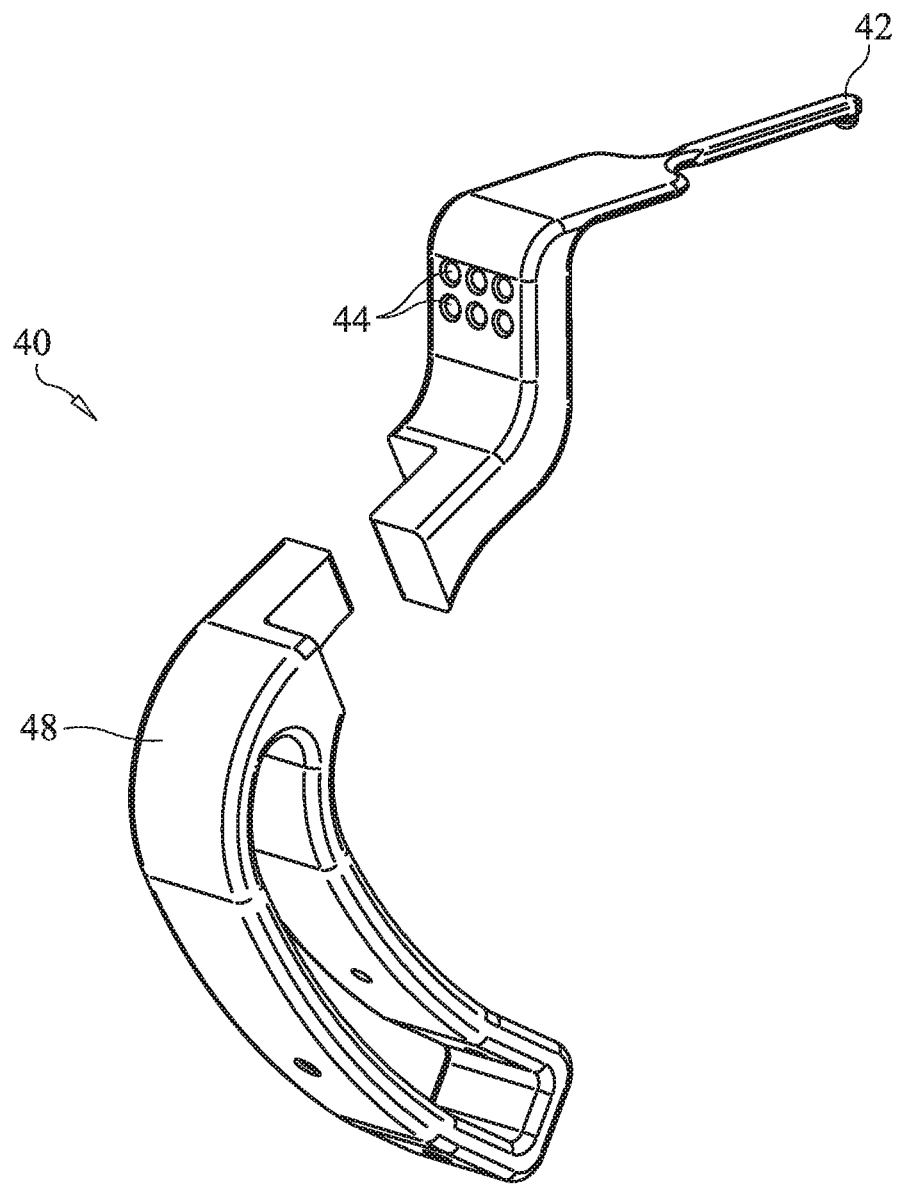
FIG. 4B shows another exemplary embodiment of the SUBCHONDROPLASTY™ guide/insertion tool or instrument.

FIG. 4B shows another exemplary embodiment of the SUBCHONDROPLASTY™ guide/insertion instrument 40. As shown, in this embodiment, the SCP™ guide/insertion instrument 40 may comprise a detachable handle 48. The detachable handle 48 may be detachable in order to facilitate its manipulation during surgery. The detachable handle 48 may be detachable based on various mechanisms that are known to those skilled in the art.

Figure 5:
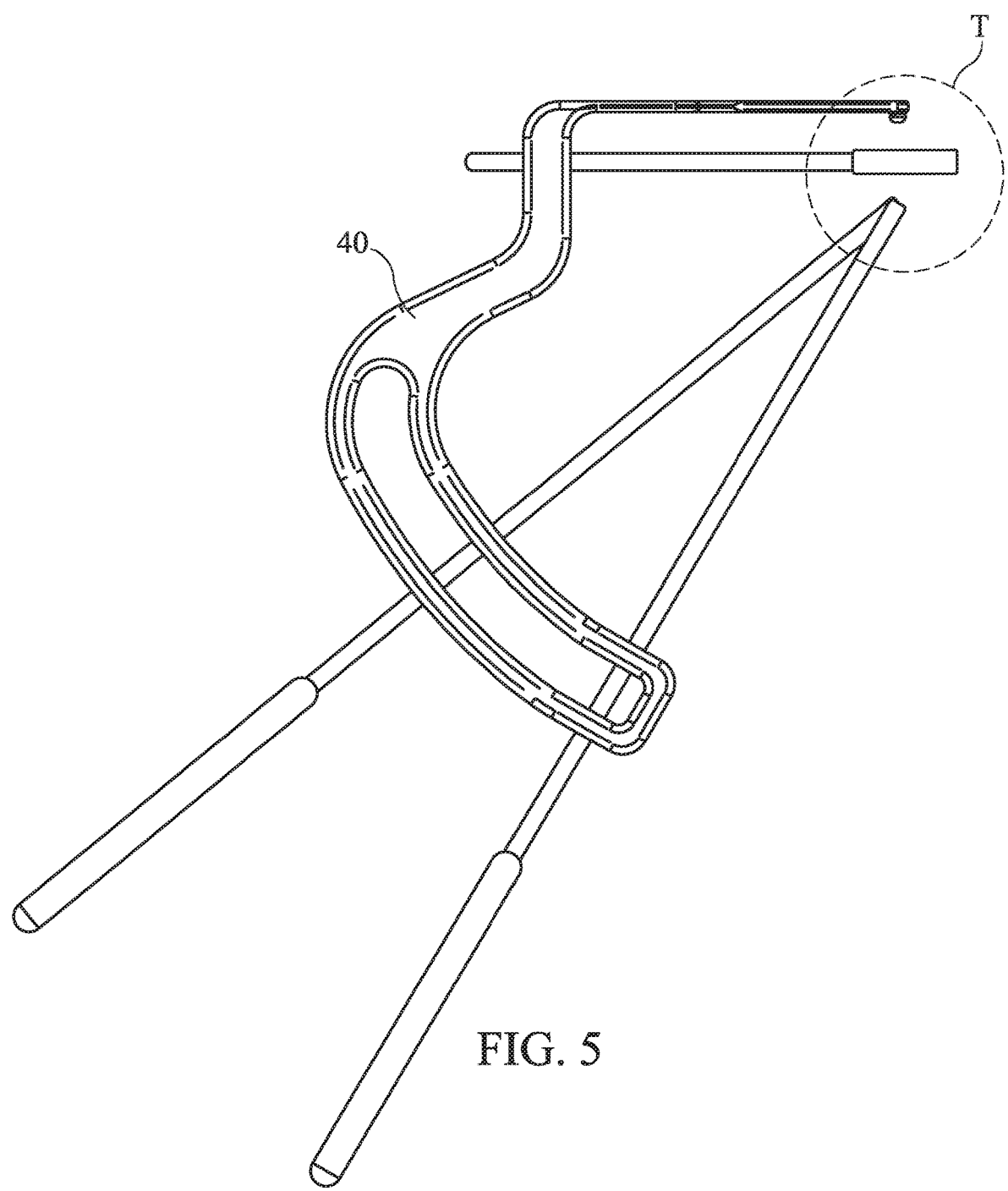
FIG. 5 illustrates a side view of a SUBCHONDROPLASTY™ guide/insertion instrument and various options of the guide/insertion instrument in use with other instruments of the kit.

FIG. 5 illustrates a side view of the SCP™ guide/insertion instrument 40 and various options of the instrument 40. As shown, the probe of the SCP™ guide/insertion instrument 40 may comprise integrated cartilage reference 42 and parallel drill/implant guide 44. The guide 44 is configured to guide a drill 70 or other tool to a location or target T indicated by the cartilage reference 42. In addition, in the embodiment shown, the curved body of the SCP™ guide/insertion instrument comprises an angular drill guide/portal 46. The guide/portal 46 may provide a set of guides/portals that converge at location T from various angles, such as 30 degrees and 45 degrees.

Figure 6:
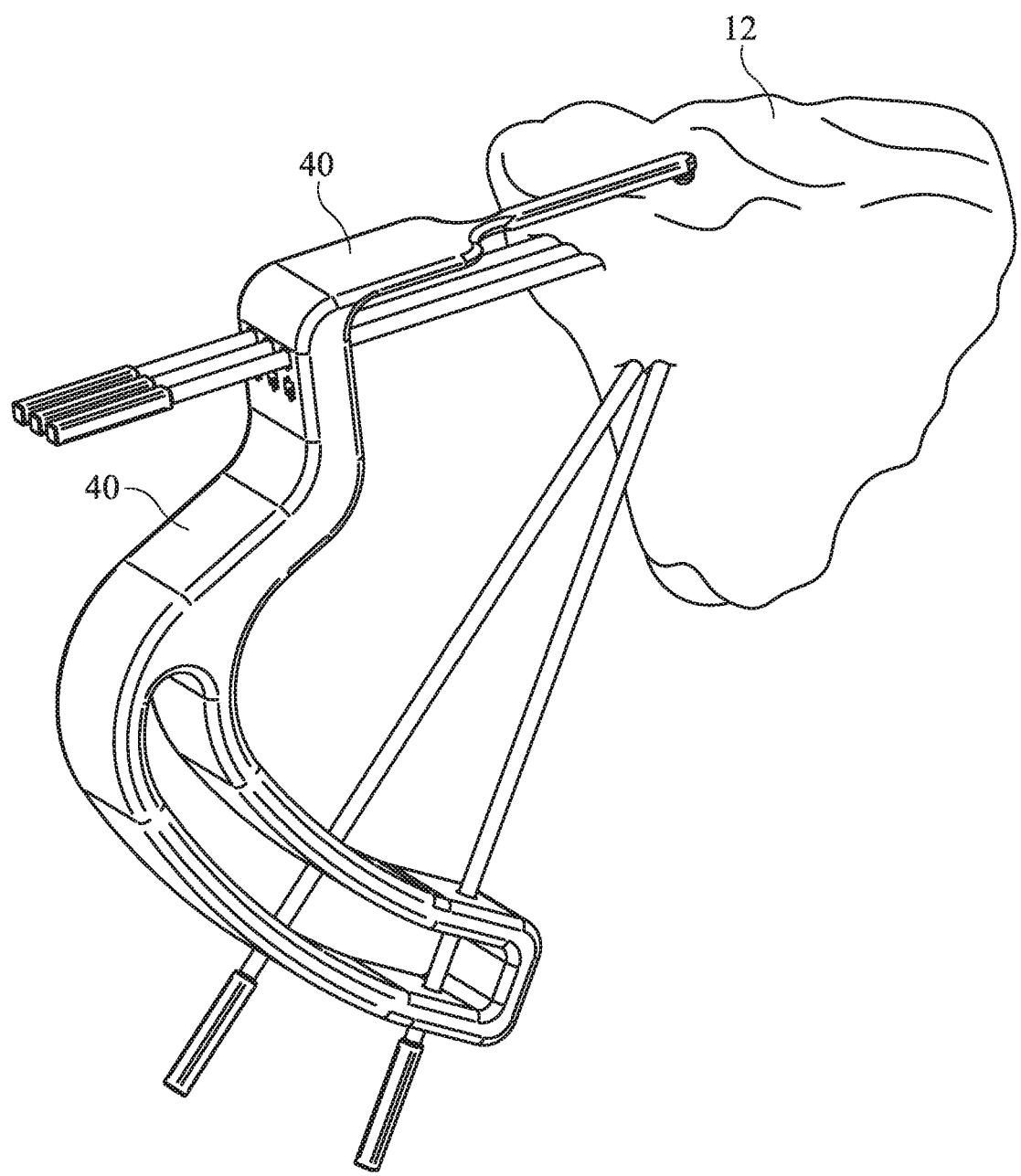
FIG. 6 illustrates a perspective view of the various options of the SUBCHONDROPLASTY™ guide/insertion instrument in use with other instruments of the kit.

FIG. 6 illustrates a perspective view of the various options of the SUBCHONDROPLASTY™ guide/insertion instrument 40. As shown, the parallel drill/implant guide 44 may comprise a series of holes/portals in a matrix configuration to help guide a drill 70 or other tool to location T.

Figure 7A:
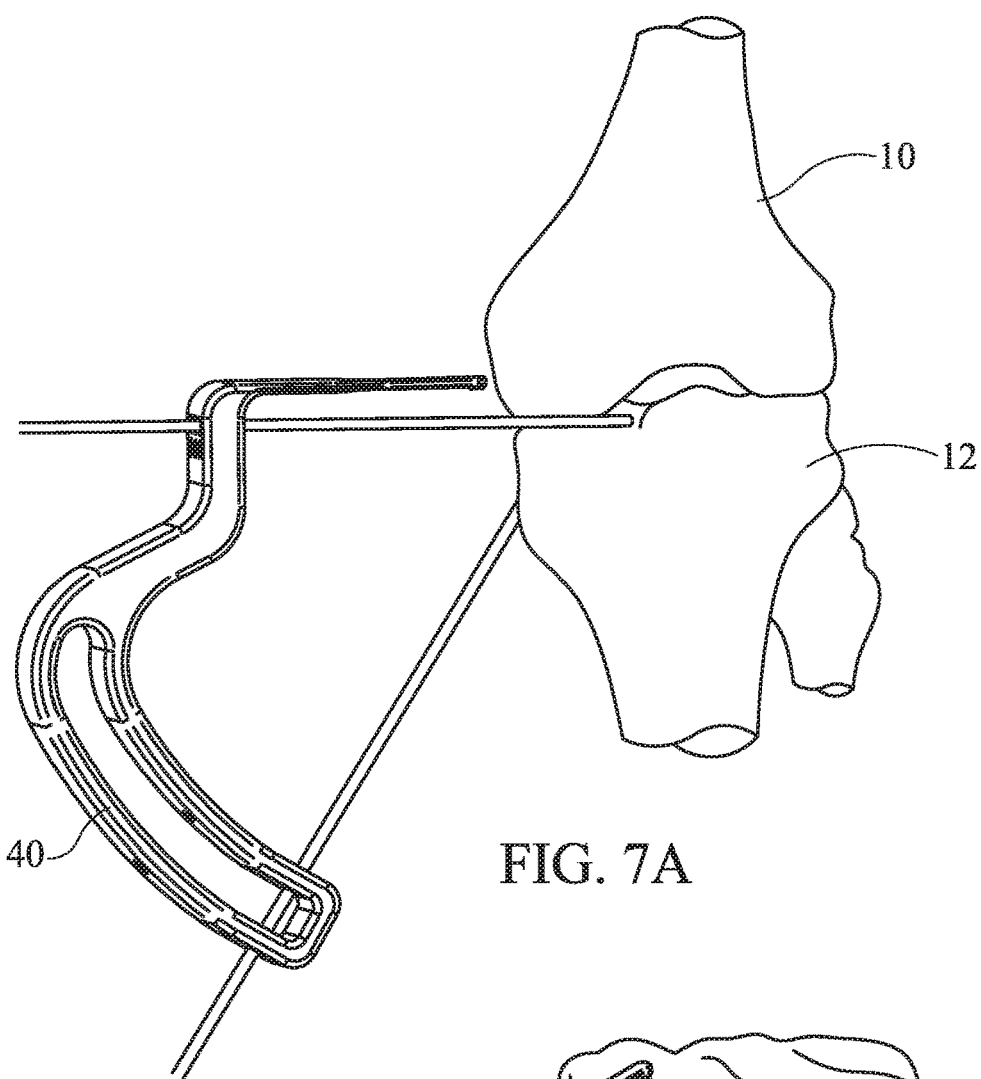
FIG. 7A shows one embodiment of a SUBCHONDROPLASTY™ guide/insertion instrument and a side view of how the guide/insertion instrument may be placed relative to a knee.
Figure 7B:
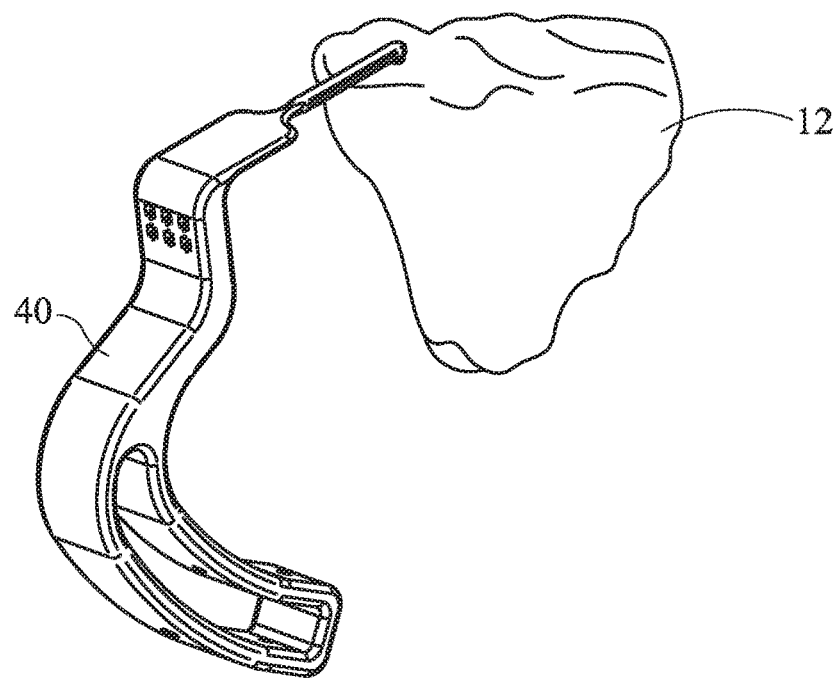
FIG. 7B shows another embodiment of a SUBCHONDROPLASTY™ guide/insertion instrument and a perspective view of how it may be placed relative to a knee.

FIG. 7A shows another embodiment of a SUBCHONDROPLASTY™ guide/insertion instrument 40 and side view of how it may be placed relative to a knee during surgery. FIG. 7B shows the SUBCHONDROPLASTY™ guide/insertion instrument 40 and a perspective view of how it may be placed relative to a knee.

FIGS. 8, 9A-9J, 10A-10B, 11A-11C illustrate a method of treating a knee based on embodiments of the present invention. As noted, medical imaging, such as an MRI, is taken of the knee of a patient suffering from arthritic pain. A bone marrow lesion, such as a subchondral insufficiency fracture 92, is identified and located on the MRI. The fracture size, volume and orientation are determined from the image, and based on the findings, the recommended volume of bone void filler is determined from the volume assessment tool. The SCP™ template, shown in FIGS. 3A and 3B, is a transparency with a plurality of curved lines between two intersecting straight lines. In use, the template 50 is placed over the MRI image to determine the placement of the SCP™ guide/insertion instrument 40, the appropriate location for the fixed bone portal 62, and the resulting depth to the fracture.

Figure 8:
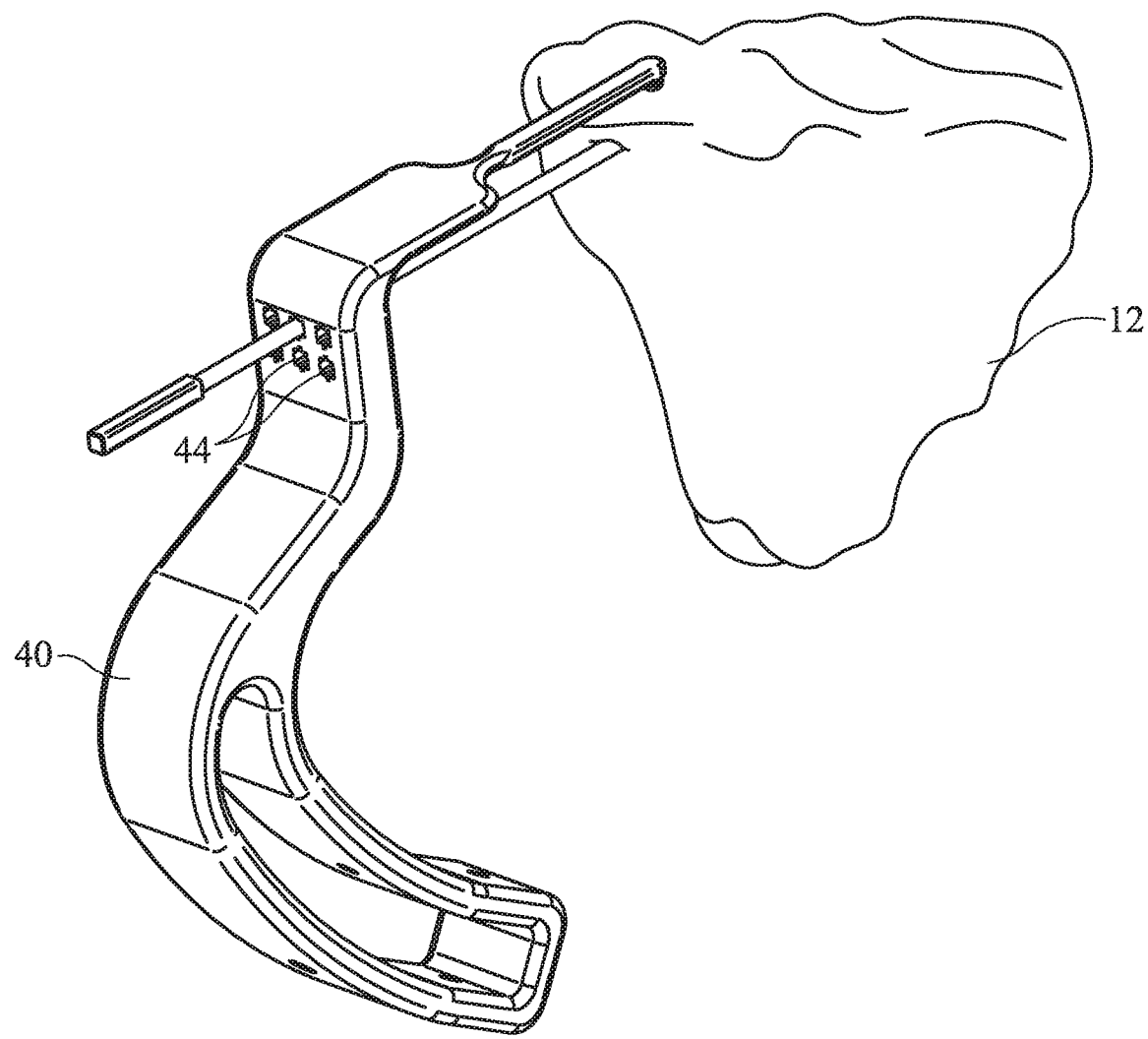
FIGS. 8, 9A-9J, 10A-10B, and 11A-11C illustrate a method of treating a knee based on embodiments of the present invention.

Referring now to FIG. 8, the SCP™ guide/insertion instrument 40 may be positioned such that the location T of the cartilage guide 42 is in on or adjacent to the bone marrow lesion of interest. In use, the SCP™ guide/insertion instrument 40 is placed proximate to the joint. The probe may be visually placed on the articular cartilage, for example, using arthroscopy. If present, any cartilage defect can be used to assist probe placement.

The SCP™ guide/insertion instrument 40 helps determine the access point and angle for the K-wire (included in the kit 20), which may be used by the surgeon. For example, in some embodiments for treating a patient's knee, the SCP™ guide/insertion instrument 40 is configured to treat subchondral bone that s within 5 mm below the tibial surface. In some embodiments, the SCP™ guide/insertion instrument 40 has a planar, rasped tip for contacting and gripping the articular surface of the knee joint without damaging the cartilage.

Using parallel drill/implant guide 44, a surgeon may then drill parallel, for example, to the articular surface of a patient's knee. In some embodiments, the surgeon drills through or adjacent to the bone marrow lesion.

Figure 9A:
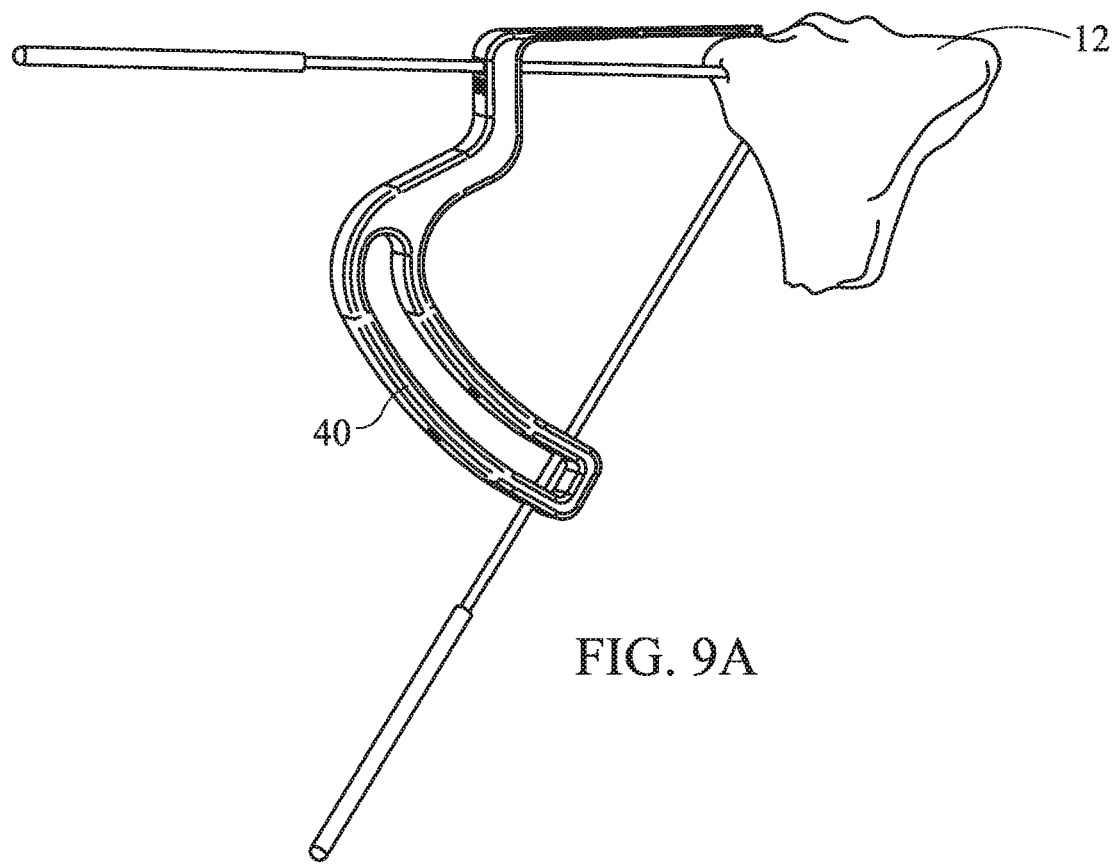

Referring now to FIG. 9A, the surgeon may then drill at an angle to location T of the bone marrow lesion 92 via angular drill guide/portal 46. The surgeon may select the angle of approach based on a variety of factors, such as the location of the bone marrow lesion, size of the lesion, access to the knee, etc. While the SCP™ guide/insertion instrument 40 is held in place, a K-wire is inserted through the lumen in the adjustable arm and into interior of the bone. Fluoroscopy may be used to verify the position and depth of the wire with respect to the fracture 92. The SCP™ guide/insertion instrument 40 may then be removed, but the K-wire retains the angle and depth to the fracture 92.

Figure 9B:
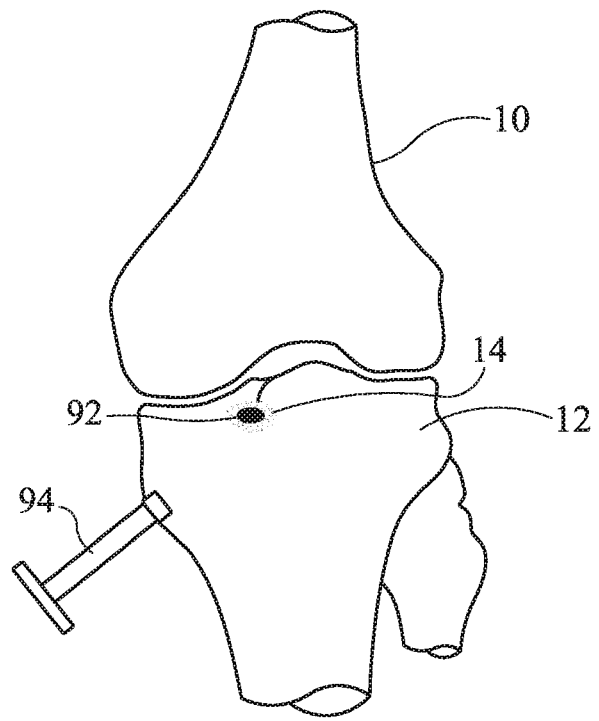
Figure 9C:
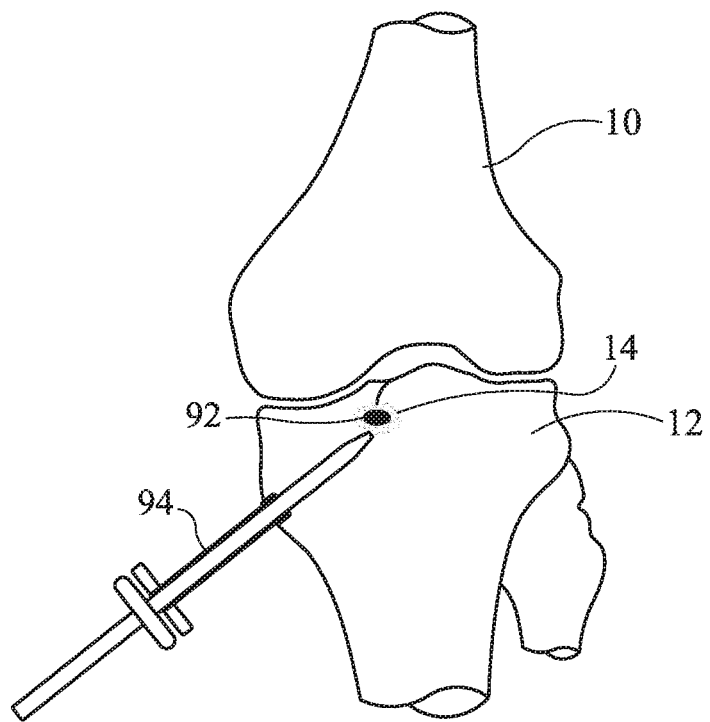
Figure 9D:
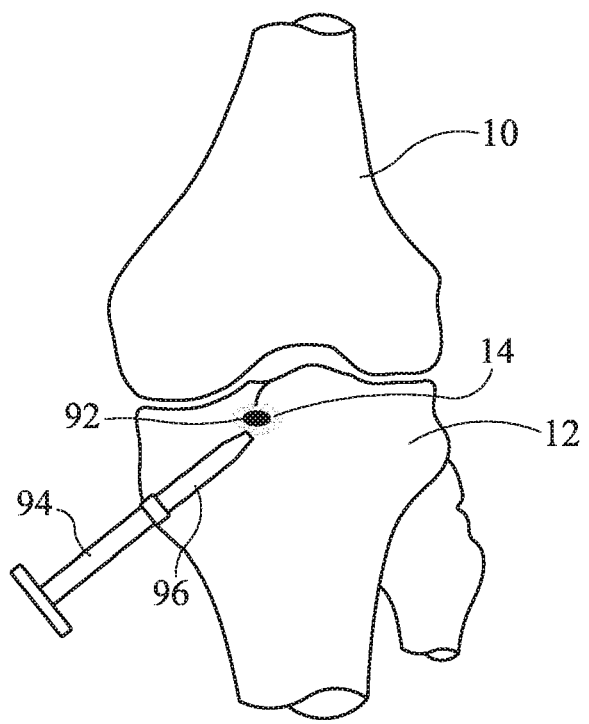

FIGS. 9B-9D illustrate in further detail how a surgeon may drill at an angle to a bone marrow lesion 92. As shown, the surgeon may install a bone portal 94, for example, using the SCP™ guide/insertion instrument 40 (not shown).

In use, the SCP™ guide/insertion instrument 40 is placed proximate to the joint. Based on the information determined from the SCP™ template, the probe tip of SCP™ guide/insertion instrument 40 is placed on a target location on the articular surface of the knee joint, i.e., in or adjacent to the bone marrow lesion. As noted above, in order to treat knee pain, the bone marrow lesion 14 may be a meniscal defect associated with an underlying subchondral insufficiency fracture 92.

The guide/insertion instrument 40 is used to aim a bone portal angle and to set the bone portal depth stop based on the information determined from the SCP™ template. The SCP™ guide/insertion instrument 40 may then be removed and the bone portal retains the angle to the fracture location. During surgery, the bone portal may also hold or steady the SCP™ guide/insertion instrument 40.

The bone portal 62 (included in the kit 20) provides an entry point n the bone for an instrument to gain access to the interior of the bone and to the subchondral insufficiency fracture 92. The bone portal 62 may be a single component design having an elongate body. The distal end of the body may include external threads for anchoring the portal 62 to the cortex of the bone. In some embodiments, the portal 62 has an outer diameter of approximately 8 mm. The size of a particular bone portal 62 is selected to support the cortex and prevent possible damage and weakening of the surrounding cortex. The body of the bone portal 62 has a lumen for receiving an instrument therein and a length that allows for an accurate trajectory to the bone marrow lesion 14. The proximal end of the body has a depth stop for limiting the extent an instrument received within the lumen may be inserted into the interior of the bone. To facilitate the ease of implementing the SUBCHONDROPLASTY™ treatment, the bone portal 62 may serve as a working channel, enabling a multitude of instruments to pass through the same access point.

In use, the bone portal 62 can be threadedly anchored to the bone cortex at a location determined from the MRI template. As shown, the bone portal 62 is installed at an angle perpendicular to the bone cortex, resulting in better coupling. Alternatively, the surgeon may use an adjustable bone portal 62 that allows for repeated entry into the bone for multiple fractures to be treated with a single bone portal insertion. The portal 62 may be made of a resorbable material, in which case it could provide as an implant left in the cortex after the SCP™ procedure is completed. Furthermore, the bone portal 62 may be radiolucent and have at least one marker for identification under imaging.

The surgeon may then drill through the SCP™ guide/insertion instrument 40 via angular drill guide/portal 46 (not shown) to create a bone cavity 96 to bone marrow lesion (as shown in FIG. 9D). The drill may be a cannulated drill 70, for example that is used over the K-wire to enlarge the channel to the fracture 92. Other bore creation devices known in the art may be used, including biopsy needles, punches, burrs, reamers, rongeurs and tamps, as well as other types of drills.

Figure 9E:
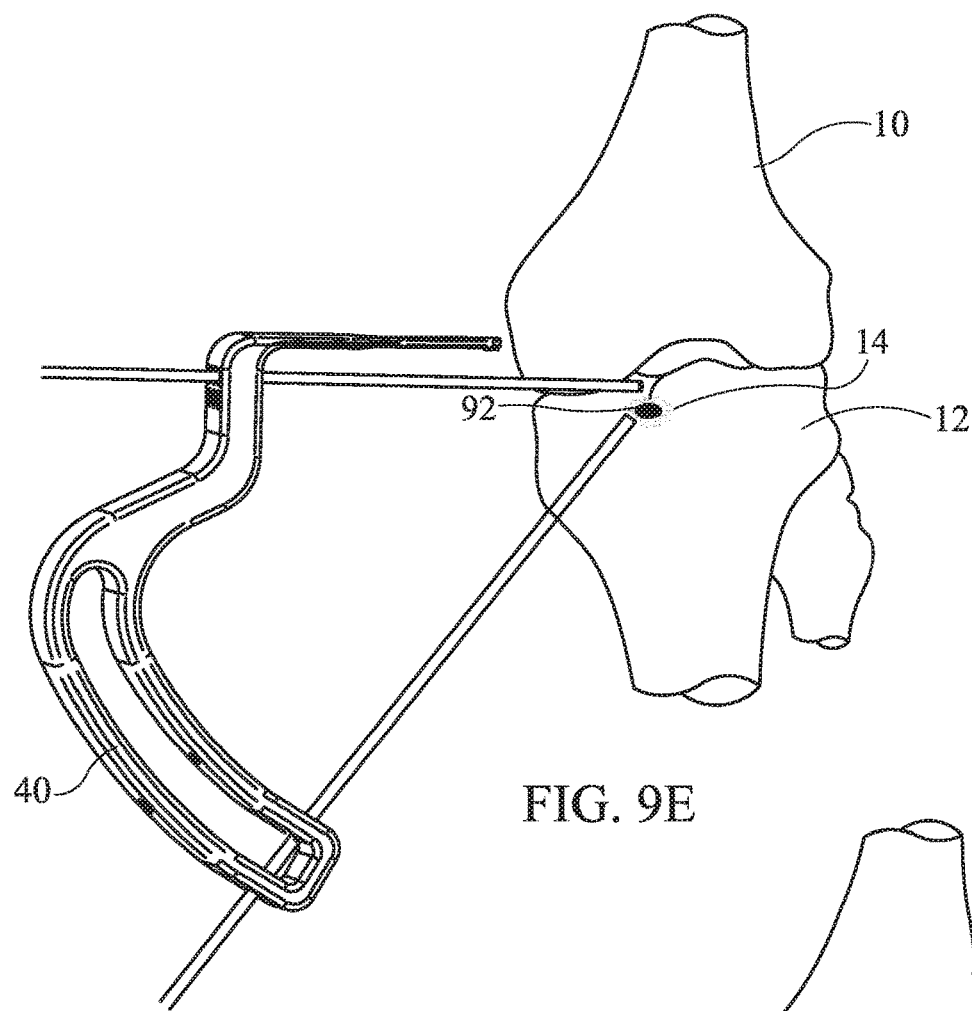

FIG. 9E illustrates how the surgeon may then employ a Kirschner wire or K-wire at the site of bone marrow lesion 92. Alternatively, FIG. 9F shows the use of an adjustable bone portal 98 that allows the surgeon to select one or more angles provided by angular drill guide/portal 46 or, for example, to treat multiple sites.

Figure 9F:
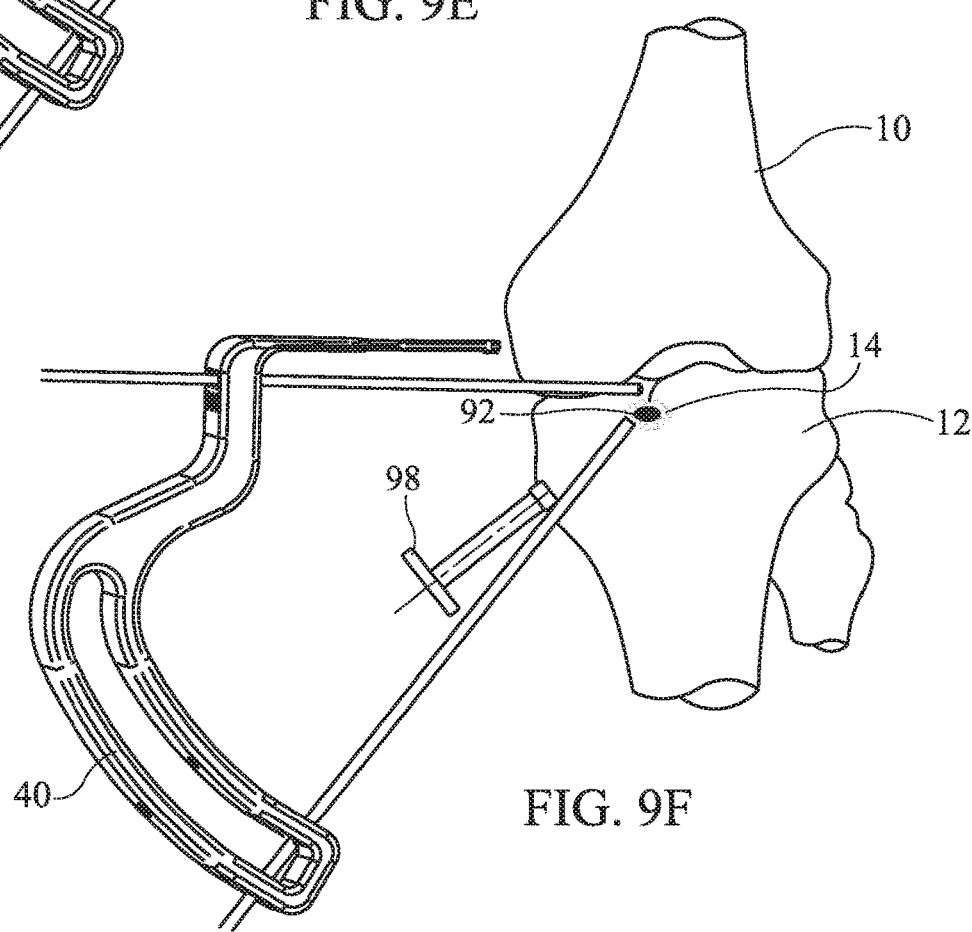
Figure 9G:
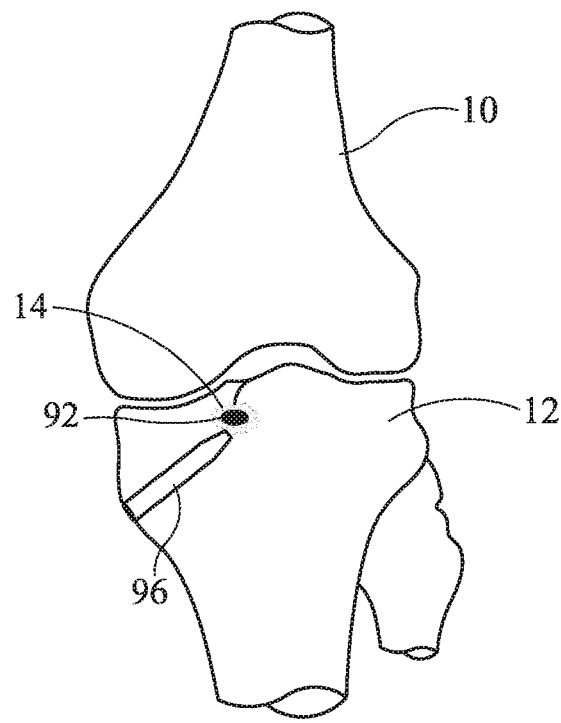
Figure 9H:
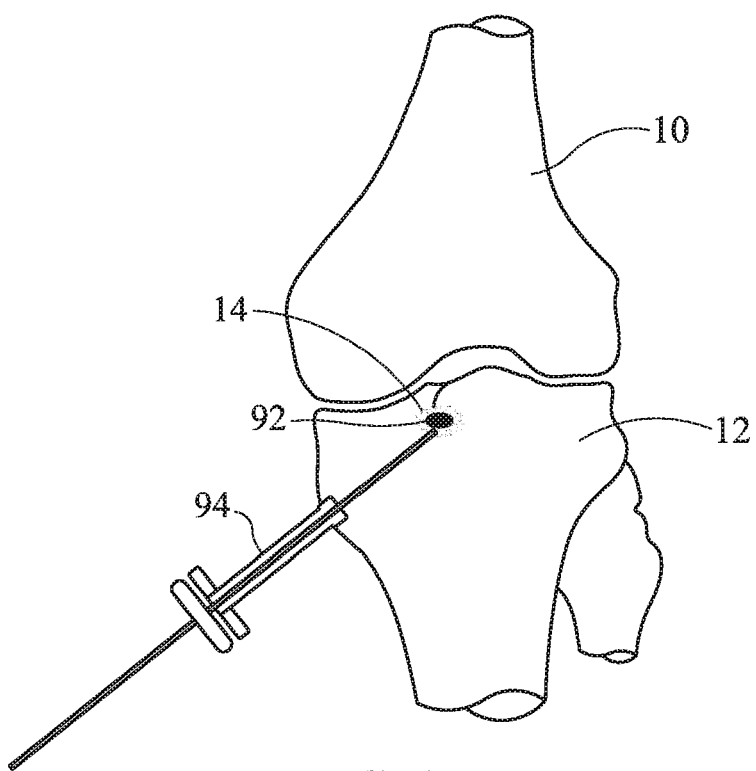
Figure 9I:
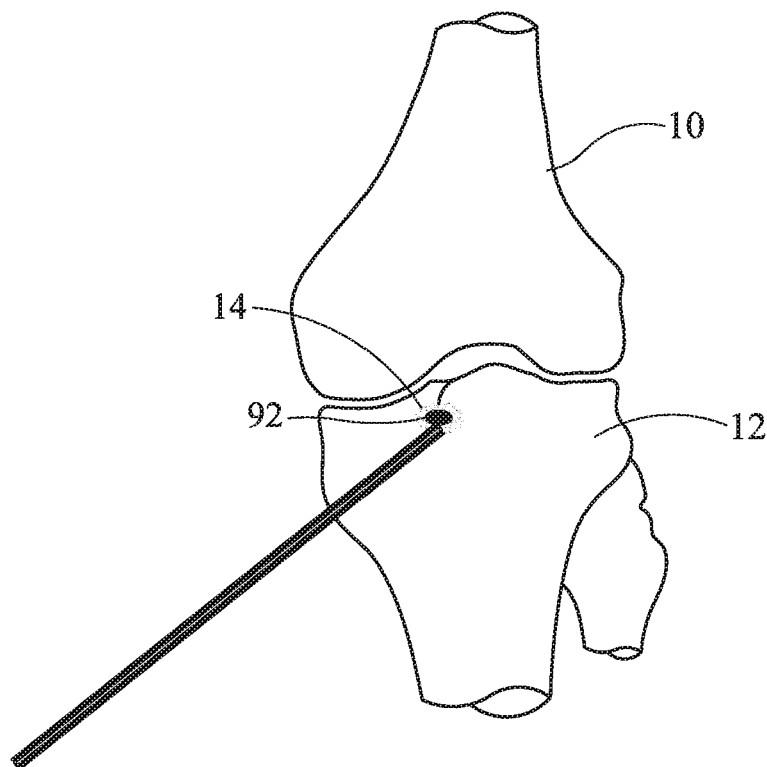
Figure 9J:
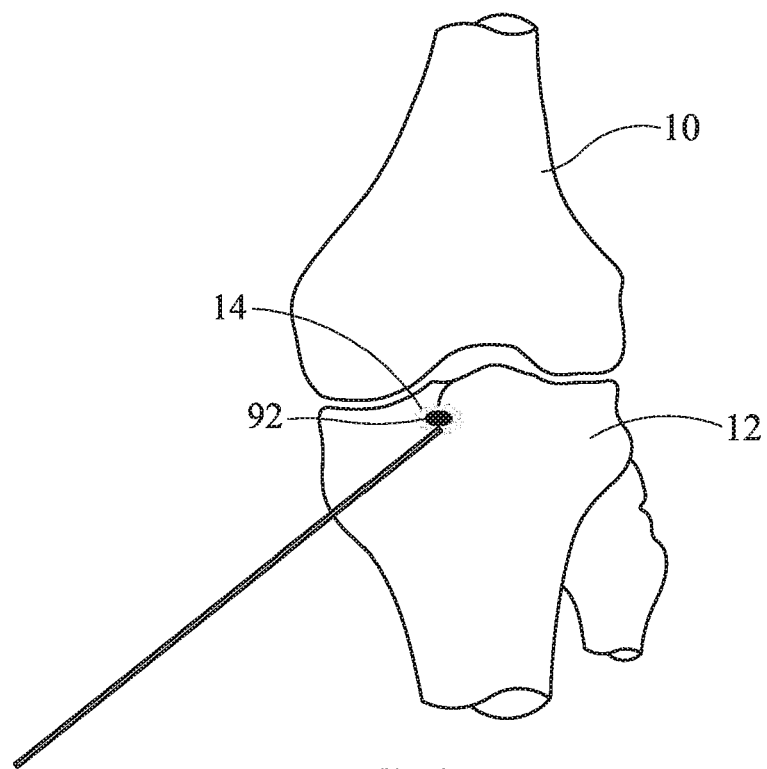

The adjustable bone portal shown in FIG. 9F may be included in the kit 20 to provide an entry point in the bone for different instruments to gain access to the interior of the bone and to a subchondral insufficiency fracture 92, as previously mentioned. In general, the adjustable bone portal has a body component and base component. The base component includes external threads for anchoring the portal to the cortex of the bone and a central opening for receiving the body component. The outer diameter of the base component is approximately 8 mm, selected to support the cortex and prevent possible damage and weakening of the surrounding cortex with a portal with a larger diameter. The body component may have a lumen for receiving different instruments, and a length that allows for an accurate trajectory to the defect. A proximal end of the body component has a depth stop for limiting the extent an instrument received within the lumen may be inserted into the interior of the bone. The depth stop may be adjusted according to the depth of the defect within the bone, as measured from the entry point.

In some embodiments, adjustability of the bone portal is achieved through a ball-and-socket arrangement between a socketed central opening in the base component and a ball shaped distal end of the body component. A lock mechanism can be provided to maintain the base and body components in a desired position relative to each other. In another embodiment, adjustability of the bone portal is achieved through a conically shaped central opening in the base component. A locking mechanism can be provided to maintain the base and body components in a desired position relative to each other.

FIGS. 9G-9J illustrates the various ways that a surgeon may treat a knee via bone cavity 96. A cavity creation device is used after a bore creating device is removed to leave an enlarged channel to the fracture, and prior to the bone void filler being prepared As shown, the surgeon may use a K-wire with a depth stop (included in the kit 20) to create an access channel to the subchondral insufficiency fracture 92. As shown in FIG. 9G-9J, the K-wire is inserted through the lumen of the bone portal body to the desired depth, which will be reached when the K-wire depth stop contacts the bone portal body depth stop. The K-wire is prevented from being advanced through the articular surface. Fluoroscopy may be used to verify the K-wire position and depth with respect to the fracture. If placement is incorrect, the K-wire can be retracted and the bone portal readjusted. The K-wire 64 is then removed.

The surgeon may use a bore creation device (also included in the kit 20) to enlarge the access channel created by the K-wire 64 to the fracture. The bore creation device can be an 8-gauge biopsy needle, a core punch, or a fenestrated drill. Each can be provided with a depth stop to prevent penetration through the articular surface of the bone. Other bore creation devices known in the art may be used, including burrs, reamers, rongeurs and tamps, as well as other types of biopsy needles, punches and drills. A cavity creation device in the form of a burr, for example, is inserted through the lumen in the bone portal to the desired depth and is manually moved or activated to create a cavity. Depending on the device used, this may be accomplished by cutting bone, compressing bone, or a combination.

As shown, the surgeon may use a cannulated drill, for example, being inserted through the lumen of the bone portal body until the drill depth stop contacts the bone portal body depth stop. The drill is prevented from being advanced through the articular surface. The drill is then removed, leaving an enlarged channel 96 to the fracture 92.

In another embodiment, a series of cannulas or bone dilators of progressively increasing diameter may be provided. The cannulas or dilators may be used to progressively bore concentric openings within the subchondral bone.

Figure 10A:
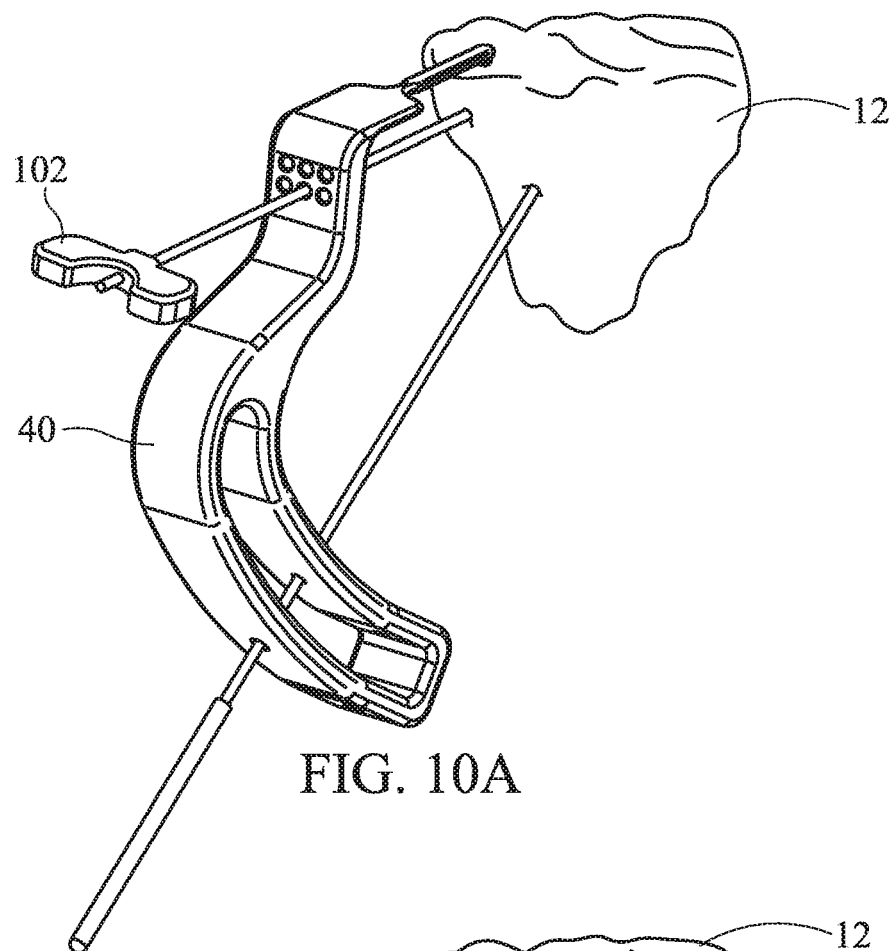

FIG. 10A illustrates another step that a surgeon may perform to treat a patient's knee. In particular, the surgeon may inject bone void filler, such as calcium phosphate (CaP) or a bone cement, such as a low viscosity Poly-methyl methacrylate ("PMMA"). During surgery, an injection catheter 66 is filled with a volume of the bone void filler, which was determined from the volume assessment tool (included in the kit 20). FIG. 10A shows the injection catheter 66 being inserted and sealed to the bone portal. Cement in the catheter 66 prevents bone shards and debris from clogging the catheter 66. Under fluoroscopy, the bone cement is injected from the catheter 66 into the subchondral insufficiency fracture 92 using a syringe 68 with volume and rate controls. The syringe 68 provides tactile feedback as the bone cement is dispensed to fill the fracture and then interdigitate with the immediately surrounding cancellous bone. The catheter 66, syringe 68 and bone portal 62 may then be removed.

In order to prevent bone void filler from leaking out of the hole that remains in the cortex after removal of the bone portal, a portal hole plug (provided in the kit 20) may be used. Alternatively, the bone that was removed using the bore creation device during the channel enlargement step may be sized and shaped as a plug to fill the portal hole. Of note, the injection of a bone void filler can be before or after the implantation of reinforcing member 16. If desired, the bone marrow lesion or edema may be aspirated prior to insertion of the implant or infusion of the bone void filler. This aspiration step may be performed through the angular drill guide/portal 46, and suction may be performed through the parallel drill/implant guide 44.

Figure 10B:
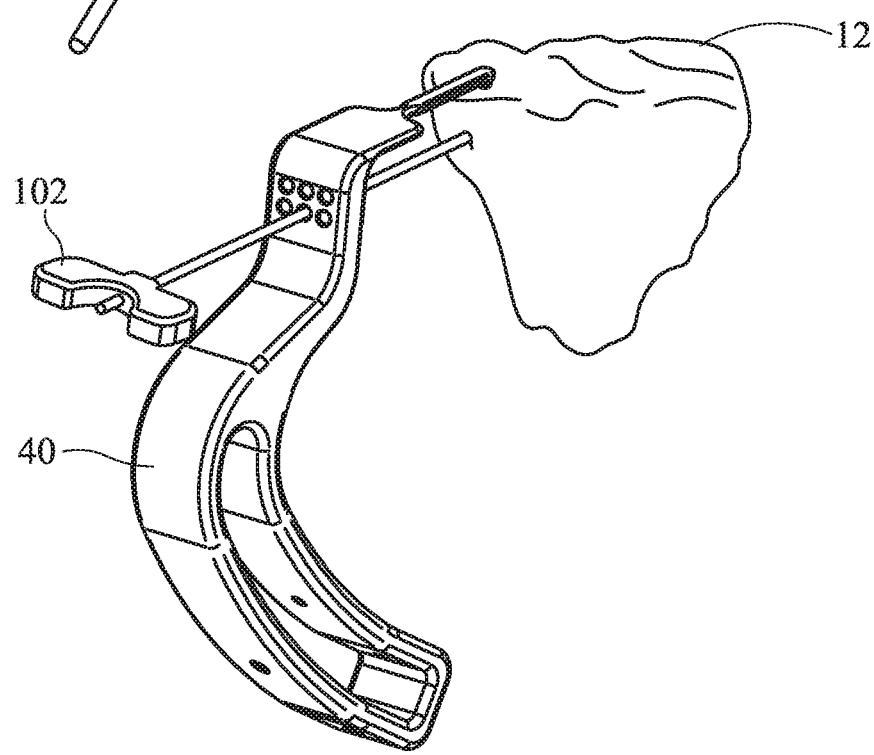

For example, as shown, an 8-gauge needle 102 may be guided via parallel drill/implant guide 44 in or adjacent to the bone marrow lesion. FIG. 10B illustrates another view of the surgeon injecting CaP cement via the parallel drill/implant guide 44. In some embodiments, the surgeon may drill one or more holes at various locations. In addition, the surgeon may leave the drill bits in place in order to stability the SCP™ tool guide 40.

Alternatively, the surgeon may insert one or more bone conductive pins through the SCP™ tool guide 40 and into pre-drilled holes. After the implants have been implanted, the SCP™ tool guide 40 may be removed and pins cut flush to the bone surface.

Figure 11A:
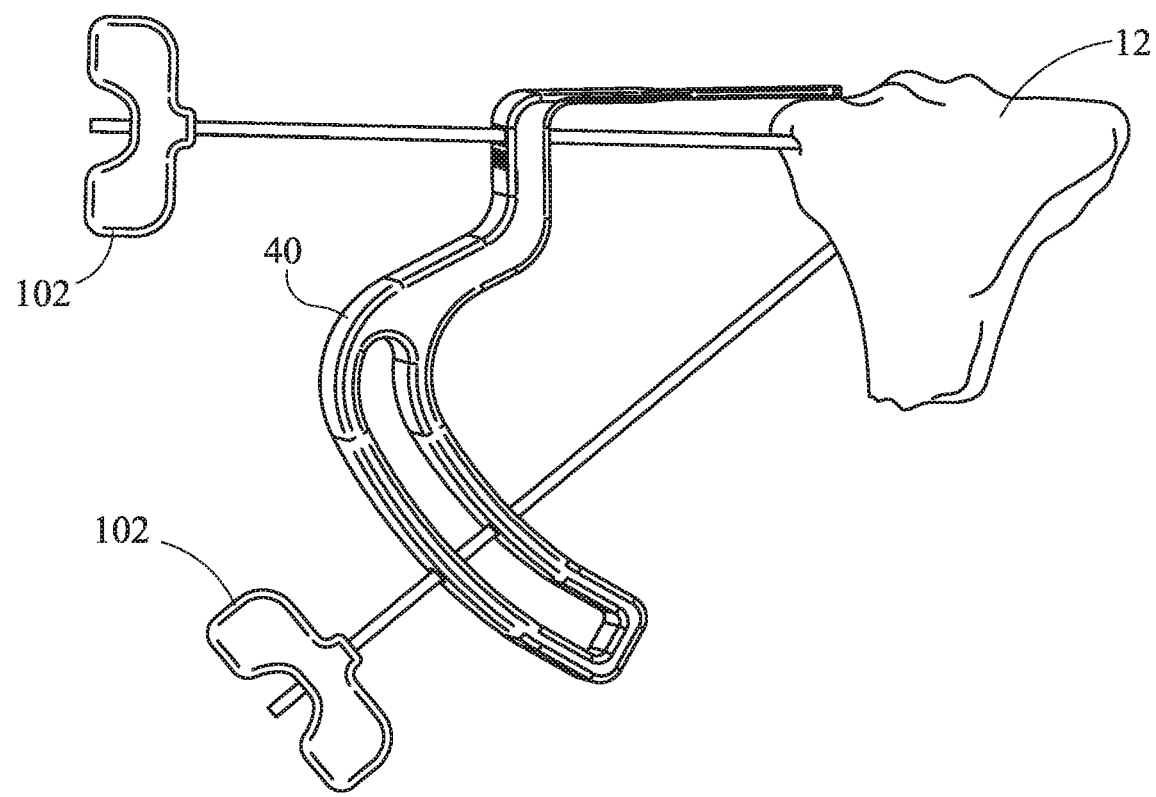
Figure 11B:
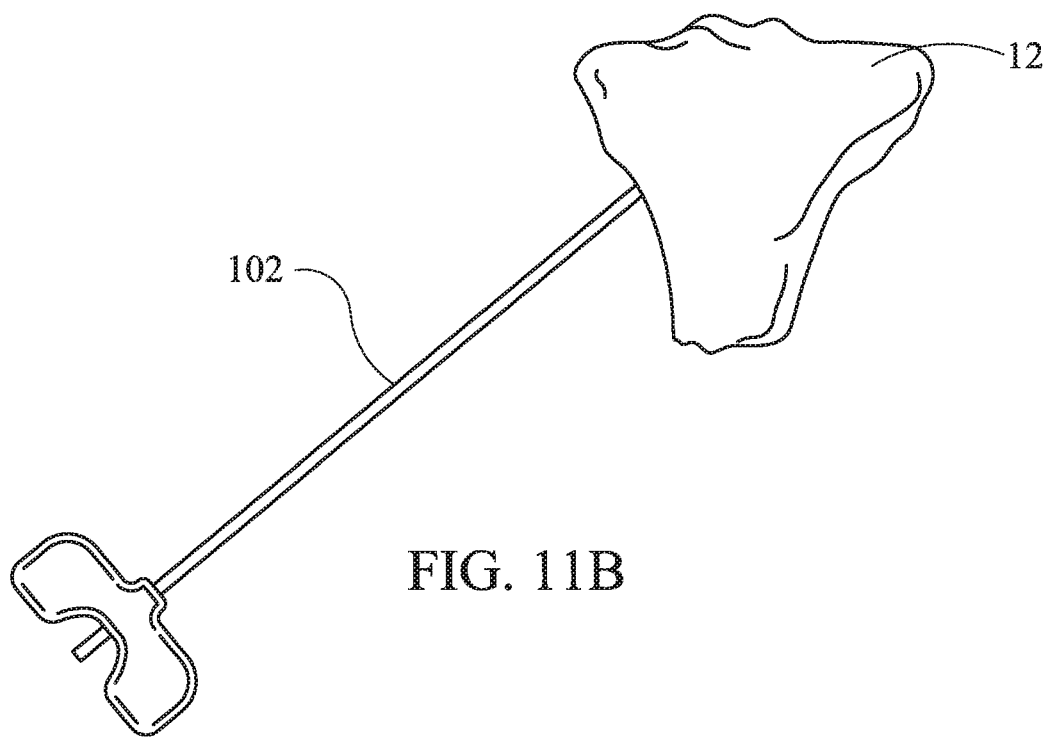
Figure 11C:
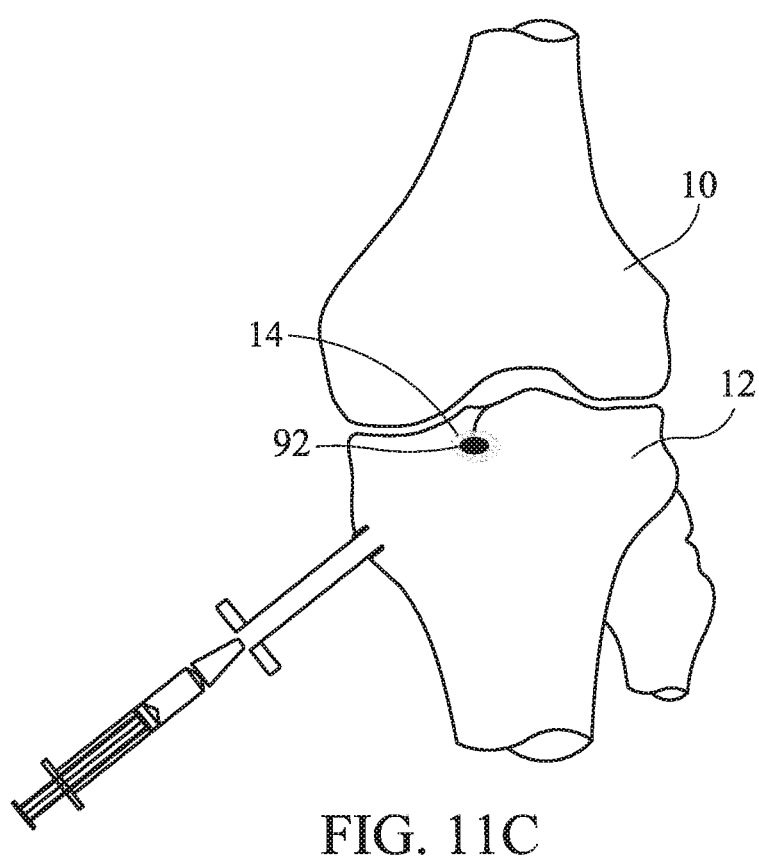

FIGS. 11A-11C illustrate another step that a surgeon may perform to treat a patient's knee. For example, FIG. 11A shows a side view of surgeon injecting CaP cement in or adjacent to a bone marrow lesion using 8-gauge needles 102. As shown, the 8-gauge needles 102 are guided using SCP™ guide/insertion instrument 40 to converge in or adjacent to bone marrow lesion. Alternatively, as shown in FIG. 11B, once the drills have been inserted, the surgeon may remove the SCP™ guide/insertion instrument 40 (not shown) and guide an 8-gauge needle 102 over the drill to inject CaP cement in or adjacent to the bone marrow lesion. For example, a catheter 66 filled with bone cement is then injected into the bone cavity 96 to fill the cavity and then any interstitial space of surrounding uncompressed cancellous bone.

Figure 13:
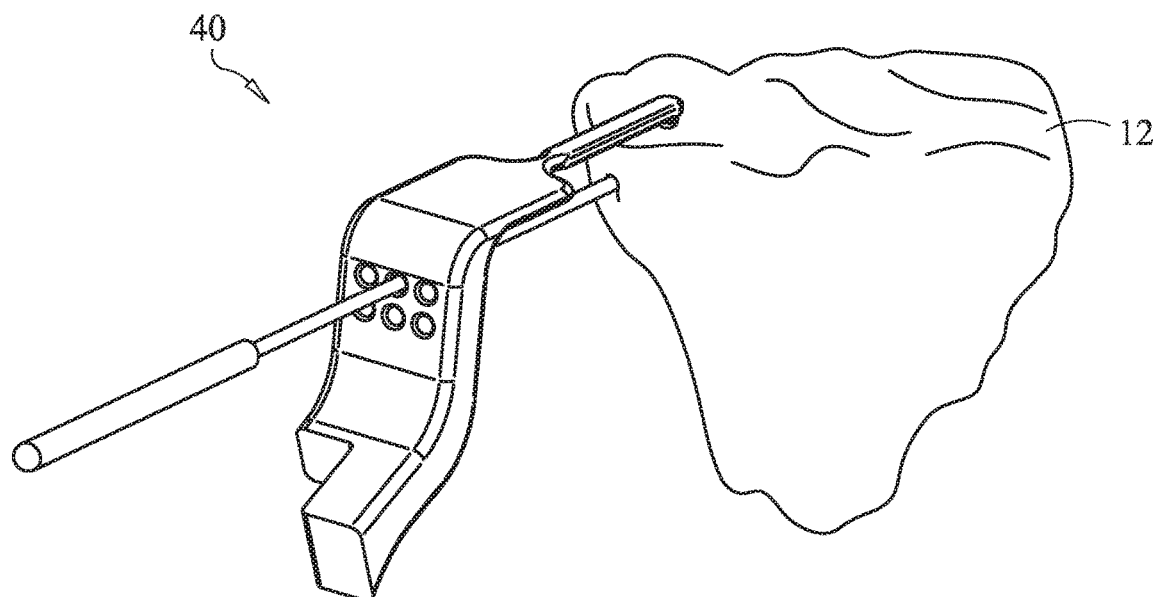

FIGS. 12-16 illustrate a method of treating a bone based on another embodiment of the present invention. In particular, as shown in FIG. 12, the SCP™ guide/insertion instrument 40 may comprise a detachable handle that the surgeon removes initially to position the guide/insertion instrument 40, for example, on the articular surface. Referring now to FIG. 13, the surgeon may then drill via parallel drill/implant guide 44 towards the site of a bone marrow lesion (not shown).

Figure 14:
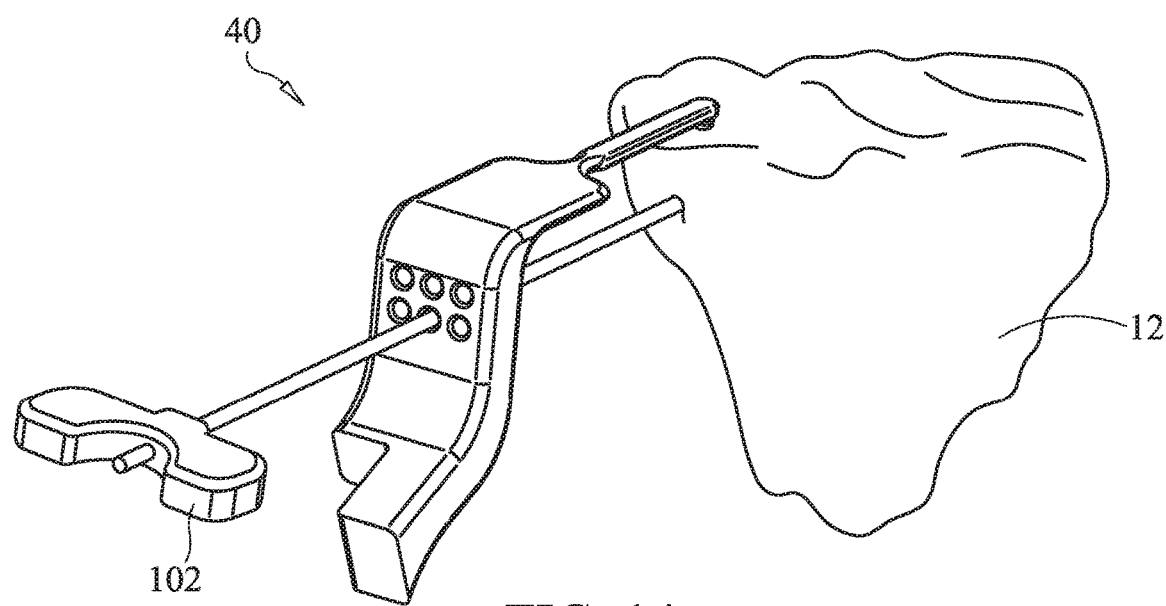
Figure 15:
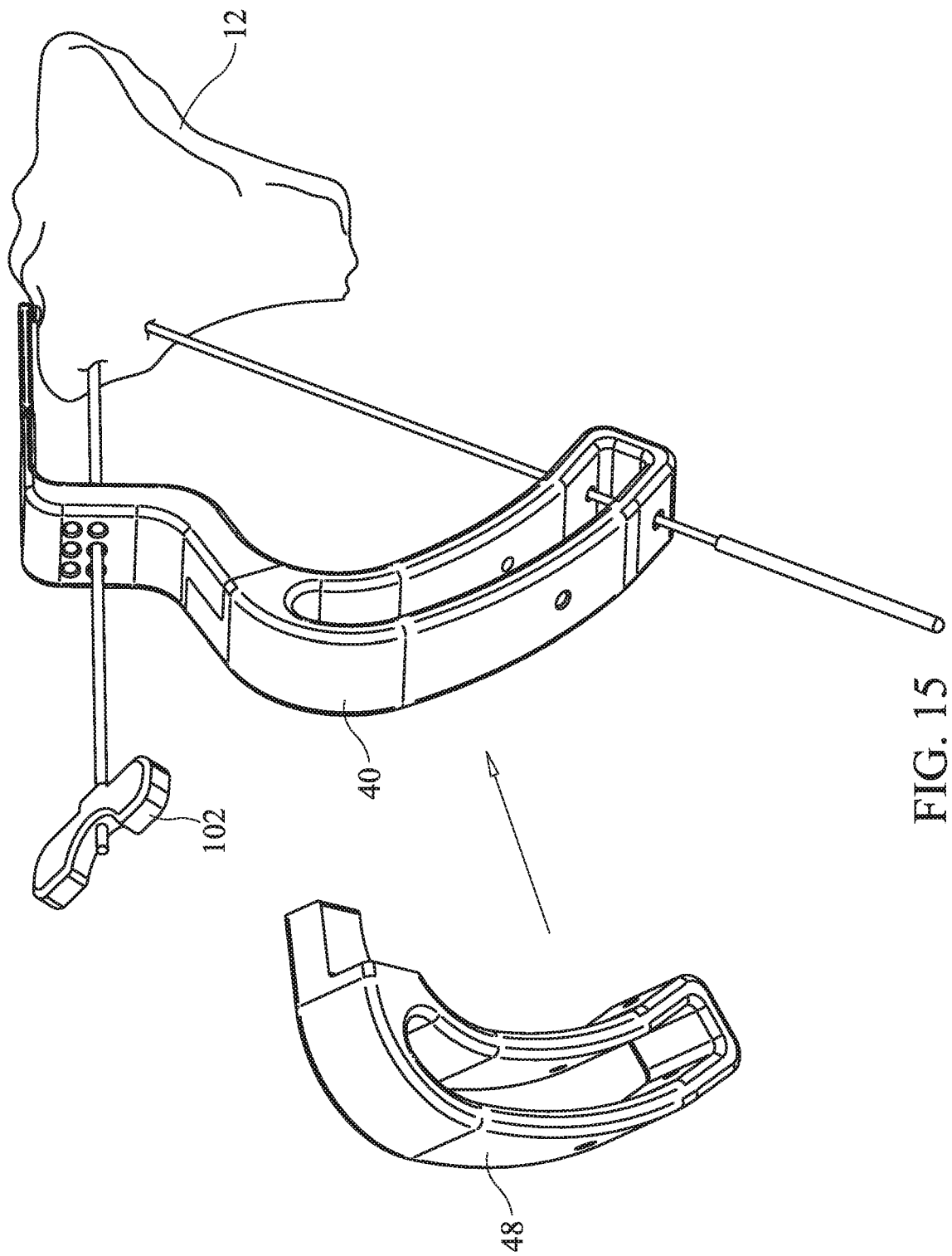
Figure 16:
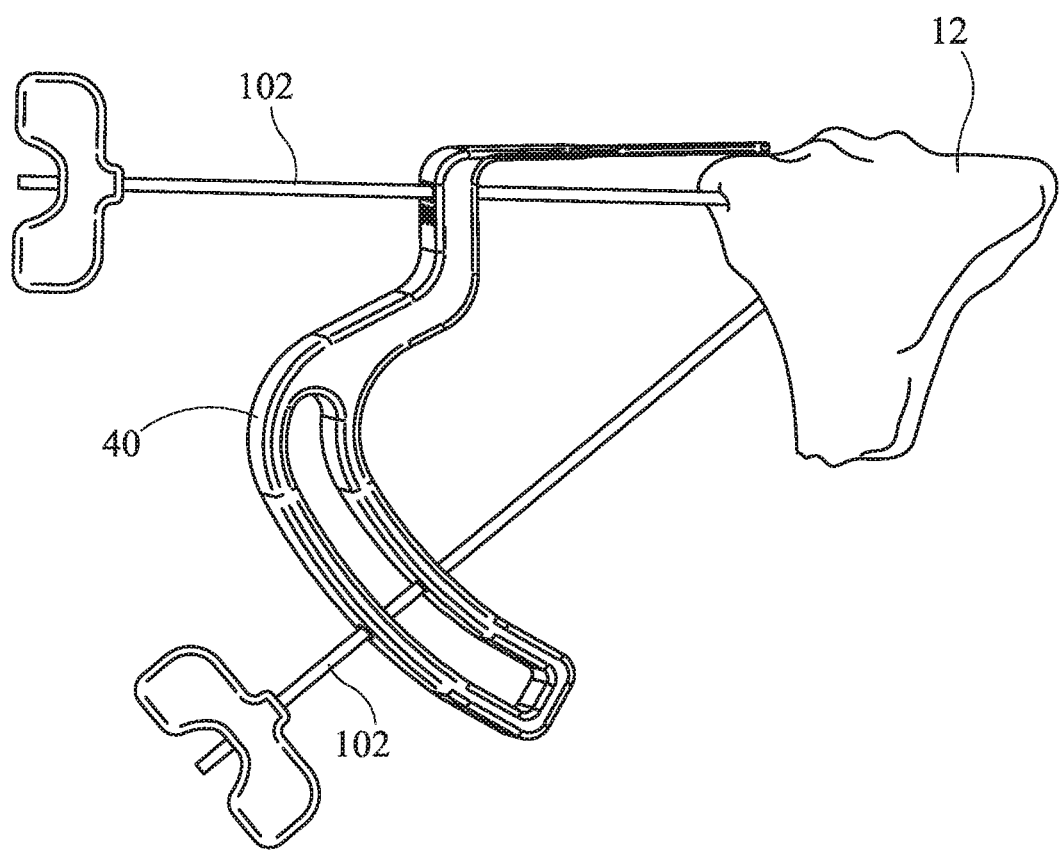

As shown in FIG. 14, the surgeon injects CaP cement using an 8-gauge needle over the drill in or adjacent to the bone marrow lesion. Next, as shown in FIG. 15, the surgeon may reattach the detachable handle 48 to the SCP™ guide/insertion instrument 40 and drill in or through the bone marrow lesion (not shown) via angular drill guide/portal 46. As shown in FIG. 16, if desired, the surgeon may then inject CaP cement using a cannula with injection port or fenestrated distal tip for target placement or dispersion of the bone void filler, or the 8-gauge needle 102, over the drill to inject CaP cement in or adjacent to the bone marrow lesion via angular drill guide/portal 46.

While the invention is described in the context of osteoarthritis of the knee, it is not limited to such condition. Other conditions that can be treated in accordance with the invention include but are not limited to osteoarthritis of joints other than the knee, such as the shoulder, hip and ankle. For example, the SUBCHONDROPLASTY™ treatment may be used to treat other joints, such as the shoulder, hip, and ankle. Moreover, in some embodiments, the SUBCHONDROPLASTY™ treatment may be coupled to other forms of joint pain treatment. For instance, in the knee, the SUBCHONDROPLASTY™ treatment may be employed in conjunction with a microfracture, arthroscopic/arthrosurface, uni-knee replacement, or partial bone resurfacing procedure. In such cases, the SUBCHONDROPLASTY™ procedure itself becomes a component in a multi-step treatment process to address the overall pain management and treatment of the joint.

Other embodiments of the invention will be apparent to those skilled in the art from consideration of the specification and practice of the disclosure provided herein. It is intended that the specification and examples be considered as exemplary only, with a true scope and spirit of the disclosure being indicated by the following claims.

What is claimed is:

1. A method of accessing a targeted site in a subchondral region of a first bone adjacent a knee joint, the method comprising:
    identifying a bone marrow lesion that is less than 10 cm from a knee joint through use of magnetic resonance imaging (MRI) of the knee joint, the bone marrow lesion occurring in a subchondral region of a first bone adjacent the knee joint, the subchondral region occurring under an articular surface of the first bone;
    locating a guide instrument adjacent the first bone, the guide instrument including a probe, the probe including an elongate portion and a tip, wherein said locating includes contacting a location on the articular surface of the first bone with the tip of the probe to establish a targeted site in the subchondral region of the first bone in and/or adjacent to where the bone marrow lesion was identified, the targeted site spaced a distance from the tip of the probe; and
    advancing an access tool through a first opening in the guide instrument and into the first bone, wherein the first opening guides the access tool to the targeted site in a first direction and in a manner that preserves an existing condition of the articular surface of the first bone, the first direction angled acutely relative to the elongate portion of the probe.

2. The method of claim 1 further comprising injecting an injectable fluid material into the targeted site.

3. The method of claim 2, wherein the injectable fluid material is left in the targeted site for becoming less fluid in the targeted site for reinforcing bone located in the targeted site.

4. The method of claim 2, wherein the injectable fluid material is left in the targeted site without also delivering and leaving a solid structural implant in the targeted site in addition to the injectable fluid material.

5. The method of claim 1, wherein the targeted site is in where the bone marrow lesion was identified.

6. The method of claim 1, wherein the targeted site is in and adjacent to where the bone marrow lesion was identified.

7. The method of claim 1, wherein the targeted site is up to 5 cm from where the bone marrow lesion was identified.

8. The method of claim 1, wherein the guide instrument is adjustable to allow for angular adjustment of the elongate portion of the probe relative to the first direction.

9. The method of claim 8, wherein the guide instrument includes a curved body section.

10. The method of claim 9, wherein the curved body section is connected to a second portion of the guide instrument through a sliding arrangement.

11. The method of claim 10 further comprising delivering bone marrow to the targeted site.

12. The method of claim 1, wherein the targeted site is within 5 mm from the tip of the probe.

13. The method of claim 1 further comprising delivering an osteogenic material to the targeted site.

14. The method of claim 1 further comprising delivering bone marrow to the targeted site.

15. The method of claim 1; wherein the bone marrow lesion is less than 5 cm from the knee joint.

16. The method of claim 1, wherein the bone marrow lesion is in a proximal tibia.

17. The method of claim 1, herein the bone marrow lesion is in a distal femur.

18. A method of accessing a targeted site in a subchondral region of a first bone adjacent a knee joint, the method comprising:
    identifying a bone marrow lesion in a subchondral region of a first bone adjacent a knee joint, the subchondral region occurring under an articular surface of the first bone;
    locating a guide instrument adjacent the first bone with a tip of a probe of the guide instrument positioned to indicate a selected landmark on the first bone and with a first opening in the guide instrument being in receipt of an access tool that is advanceable through the first opening for entry into the first bone, wherein the tip of the probe being positioned to indicate the selected landmark on the first bone establishes a targeted site in the subchondral region of the first bone in and/or adjacent to where the bone marrow lesion was identified, the targeted site spaced a distance from the tip of the probe; and
    advancing the access tool through the first opening and into the first bone, wherein the first opening guides the access tool to the targeted site in a first direction and in a manner that preserves an existing condition of the articular surface of the first bone.

19. The method of claim 18 further comprising injecting an injectable material into the targeted site.

20. The method of claim 19, wherein the injectable material is left in the targeted site without also delivering and leaving a solid structural implant in the targeted site in addition to the injectable material.

21. The method of claim 18, wherein the bone marrow lesion is less than 5 cm from the knee joint.

22. The method of claim 18, wherein the bone marrow lesion is in a proximal tibia.

23. The method of claim 18, wherein the bone marrow lesion is in a distal femur.

24. The method of claim 18, wherein the targeted site is in and adjacent to where the bone marrow lesion was identified.

25. The method of claim 18 further comprising delivering bone marrow to the targeted site.

26. The method of claim 18, wherein the probe includes a elongate portion that is angled acutely relative to the first direction.

* * * * *